(12) United States Patent
Dohi

(10) Patent No.: US 11,150,457 B2
(45) Date of Patent: Oct. 19, 2021

(54) OBSERVATION DEVICE

(71) Applicant: OLYMPUS CORPORATION, Tokyo (JP)

(72) Inventor: Masahito Dohi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/803,063

(22) Filed: Feb. 27, 2020

(65) Prior Publication Data

US 2020/0201015 A1 Jun. 25, 2020

Related U.S. Application Data

(63) Continuation of application No. PCT/JP2018/032657, filed on Sep. 3, 2018.

(30) Foreign Application Priority Data

Sep. 5, 2017 (JP) .................................. 2017-169906

(51) Int. Cl.
*G02B 21/00* (2006.01)
*G02B 21/14* (2006.01)
(Continued)

(52) U.S. Cl.
CPC ............... *G02B 21/14* (2013.01); *C12M 1/34* (2013.01); *G02B 21/0004* (2013.01); *G03B 15/05* (2013.01)

(58) Field of Classification Search
CPC ............ G02B 21/0004; G02B 21/0088; G02B 21/06; G02B 21/08; G02B 21/14;
(Continued)

(56) References Cited

U.S. PATENT DOCUMENTS 4,852,985 A 8/1989 Fujihara et al.
2016/0025299 A1* 1/2016 Yamazaki .......... G02B 27/0905
362/336
(Continued)

FOREIGN PATENT DOCUMENTS

EP 3009500 A1 4/2016
EP 3318913 A1 5/2018
(Continued)

OTHER PUBLICATIONS

International Search Report dated Dec. 4, 2018 issued in PCT/JP2018/032657.

*Primary Examiner* — Mustak Choudhury
(74) *Attorney, Agent, or Firm* — Scully, Scott, Murphy & Presser, P.C.

(57) ABSTRACT

An observation device includes an objective lens disposed below a container to collect light from a specimen; a surface light source that is disposed at a pupil position of the objective lens in the optical path of the illumination light, that causes illumination light to enter the container from below, and that can change a light emission pattern in a direction intersecting an emission optical axis, an imaging optical system that captures light from the specimen generated by the specimen being irradiated with the illumination light from the surface light source and focused by the objective lens below the container; and a controller that corrects a light emission pattern on a basis of the light emission pattern and at least one of a brightness, contrast, and the relationship between the number of pixels and the luminance of an acquired image with the light emission pattern.

11 Claims, 22 Drawing Sheets

(51) Int. Cl.
*C12M 1/34* (2006.01)
*G03B 15/05* (2021.01)

(58) Field of Classification Search
CPC . G02B 21/26; G02B 7/28; G02B 7/36; G02B 7/282; G03B 15/05; G03B 15/03; C12M 1/34; H04N 5/2256
See application file for complete search history.

(56) References Cited

U.S. PATENT DOCUMENTS

| | | |
|---|---|---|
| 2016/0108353 A1 | 4/2016 | Kimura |
| 2018/0113295 A1 | 4/2018 | Matsubara |
| 2019/0204577 A1* | 7/2019 | Faris .................. H04N 5/2256 |

FOREIGN PATENT DOCUMENTS

| | | |
|---|---|---|
| JP | S63-98619 A | 4/1988 |
| JP | 2016-077226 A | 5/2016 |
| JP | 2017-015856 A | 1/2017 |

* cited by examiner

FIG. 21

| S | θ | LIGHT AMOUNT |
|---|---|---|
| 1 | 0 | 107 |
| 2 | 30 | 5 |
| 3 | 60 | 7 |
| 4 | 90 | 6 |
| 5 | 120 | 4 |
| 6 | 150 | 18 |
| 7 | 180 | 140 |
| 8 | 210 | 120 |
| 9 | 240 | 119 |
| 10 | 270 | 110 |
| 11 | 300 | 98 |
| 12 | 330 | 101 |

FIG. 22

| BLn | ECCENTRICITY |
|---|---|
| 1 | 0.1 |
| 2 | 0.113 |
| 3 | 0.13 |
| 4 | 0.155 |
| 5 | 0.2 |
| 6 | 0.311 |
| 7 | 0.64 |
| 8 | 1.33~2.77 |

OBSERVATION DEVICE

CROSS-REFERENCE TO RELATED APPLICATIONS

This is a continuation of International Application PCT/JP2018/032657, with an international filing date of Sep. 3, 2018, which is hereby incorporated by reference herein in its entirety. This application claims the benefit of Japanese Patent Application No. 2017-169906, the content of which is incorporated herein by reference.

TECHNICAL FIELD

The present invention relates to an observation device.

BACKGROUND ART

To date, in the culturing of cells, every time the cells become confluent, the steps of removing a culture container from an incubator, removing the cells from the culture container, and seeding and culturing in a new culture container are repeated. However, there is a problem in that this operation must be performed by an observer checking the cells in the culture container in the incubator once or twice a day, which is very troublesome. To deal with this problem, there is a known observation device that is installed in an incubator in order to check the culture state of cells in a culture container (for example, see PTL 1).

CITATION LIST

Patent Literature

{PTL 1} Japanese Unexamined Patent Application, Publication No. 2016-077226

SUMMARY OF INVENTION

An aspect of the present invention is directed to an observation device including an objective lens that is disposed below a specimen container that contains a specimen and that collects light from the specimen through a bottom portion of the specimen container; a surface light source that is arranged at a pupil position of the objective lens in an optical path of illumination light to be incident on the objective lens or at a vicinity of a position conjugate with the pupil position, that makes illumination light transmitted through the bottom portion from below incident on the specimen container and can changes a light emission pattern related to a light emission position and a light emission range of the illumination light in a direction intersecting an emission optical axis, an imaging optical system that captures light from the specimen generated by the specimen being irradiated with the illumination light from the surface light source and focused by the objective lens below the specimen container; and a control unit that corrects the light emission pattern of the surface light source on a basis of a current light emission pattern of the surface light source and at least one of a brightness, contrast, and a relationship between the number of pixels and a luminance of an image acquired by the imaging optical system with the light emission pattern of the surface light source.

BRIEF DESCRIPTION OF DRAWINGS

FIG. 21 is a table illustrating an example of a number of the light emission positions on a surface light source, the angle around a center axis, and a corresponding incident light amount of an imaging element.

FIG. 22 is a table illustrating an example of a relationship between the number of light-emission positions at the black level or less and the eccentricity of a light emission position.

DESCRIPTION OF EMBODIMENTS

First Embodiment

An observation device according to a first embodiment of the present invention will be described below with reference to the drawings.

Figure 1:
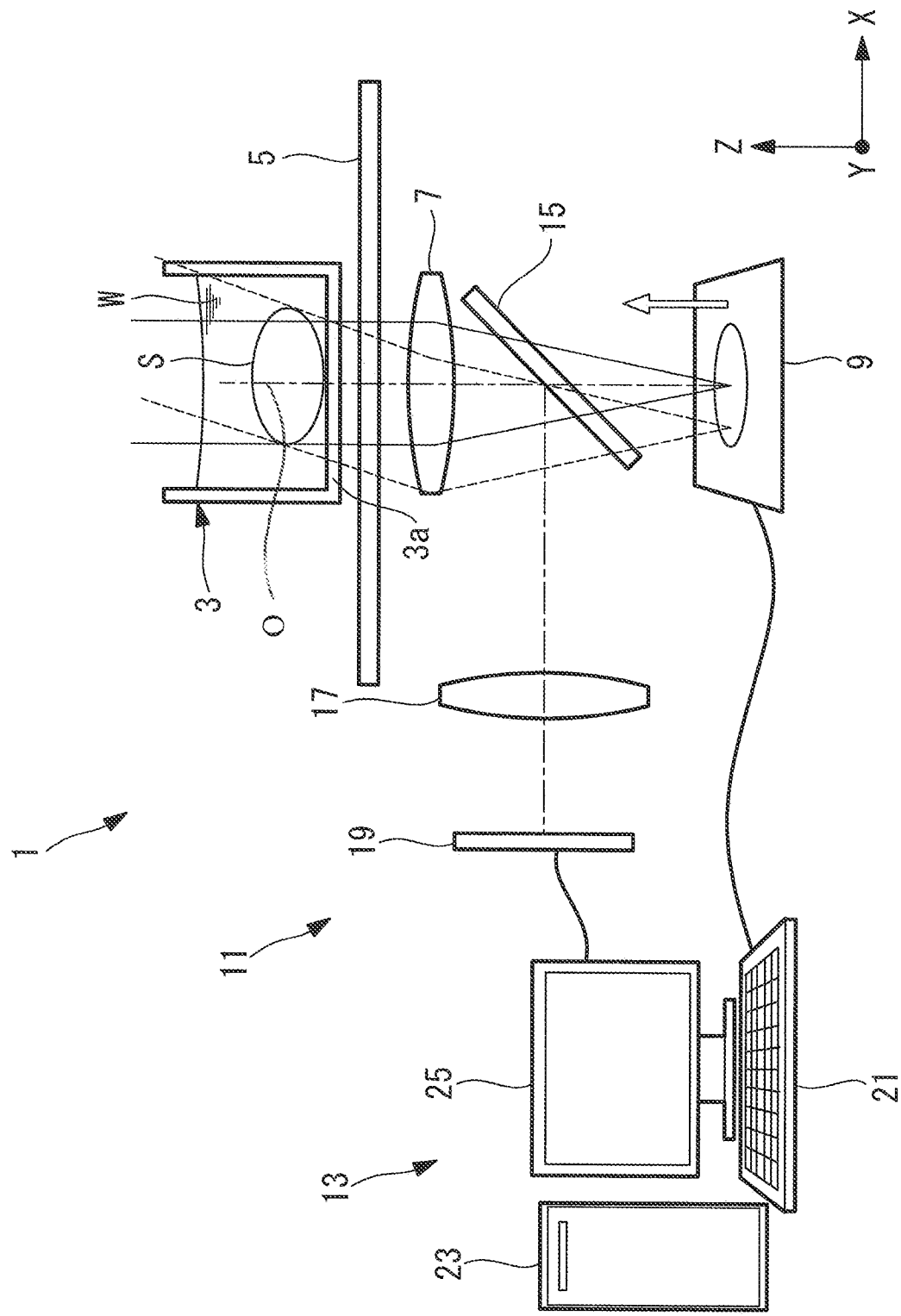
FIG. 1 is an overall configuration diagram illustrating an observation device according to a first embodiment of the present invention.

As illustrated in FIG. 1, an observation device 1 according to the present embodiment includes a stage 5 on which a specimen container 3 that contains a specimen S is mounted, an objective lens 7 that is disposed below the stage 5 and that collects observation light (light) from the specimen S, a surface light source 9 that emits illumination light upward from below the stage 5 so that the illumination light passes through a bottom portion 3a from below and enters the specimen container 3, an imaging optical system 11 that captures the observation light from the specimen S collected by the objective lens 7 below the specimen container 3, and a recording and calculation device 13 such as a personal computer (PC).

The specimen container 3 is, for example, a well container or a dish container made of an optically transparent material, and the bottom portion 3a is configured to transmit light. The symbol W indicates, for example, a solution such as a culture medium.

The stage 5 is formed of an optically transparent material and is configured so that the specimen container 3 can be mounted horizontally thereon.

The objective lens 7 is disposed vertically below the specimen S on the stage 5. The objective lens 7 irradiates illumination light from the surface light source 9 to the specimen S via the bottom portion 3a of the specimen container 3, and collects observation light from the specimen S via the bottom portion 3a of the specimen container 3 and the stage 5.

The surface light source 9 is arranged at a pupil position of the objective lens 7 in an optical path of the illumination light. As the surface light source 9, for example, a liquid crystal display in which a plurality of pixels are two-dimensionally disposed, or an LED array in which a plurality of small light emitting diode (LED) arrays are two-dimensionally disposed can be used.

In FIG. 1, a liquid crystal display serving as the surface light source 9 is exemplified, and a plurality of pixels are arranged in the X direction and the Y direction, which are perpendicular to each other, along the horizontal directions. In addition, the surface light source 9 is configured to be capable of changing a light emission pattern relating to a light emission position and a light emission range of the illumination light in a direction intersecting the emission optical axis O.

The imaging optical system 11 includes a light separating portion 15 that separates the optical path of the illumination light coming from the surface light source 9 from the optical path of the observation light coming from the specimen S, an imaging lens 17 that captures the observation light separated from the optical path of the illumination light by the light separating portion 15, and an imaging element 19 such as a charge coupled device (CCD) that captures the observation light captured by the imaging lens 17.

As the light separating portion 15, for example, a half mirror, a polarizing beam splitter, a dichroic mirror, or the like is used. In FIG. 1, for example, a half mirror or a polarizing beam splitter is used as the light separating portion 15; the illumination light from the surface light source 9 is transmitted, and the observation light from the specimen S collected by the objective lens 7 is reflected toward the imaging lens 17.

The recording and calculation device 13 includes an input unit 21 such as a keyboard for a user to input instructions, a recording and calculation unit (control unit) 23 that records data and performs arithmetic processing, and a monitor 25 that displays images and information.

The recording and calculation unit 23 includes, for example, a central processing unit (CPU), a main storage unit such as a read only memory (ROM) and a random access memory (RAM), an auxiliary storage unit such as a hard disk drive (HDD), an input unit for a user to input instructions, an output unit for outputting data, an external interface for exchanging various data with an external device, and the like (all not illustrated). Various programs are stored in the auxiliary storage unit, and the CPU reads out the programs from the auxiliary storage unit to a main storage unit such as a RAM, and executes the programs to realize various processes.

The recording and calculation unit 23 processes the image information sent from the imaging element 19 and controls the light emission of the surface light source 9 by executing a program. More specifically, the recording and calculation unit 23 corrects the light emission pattern of the surface light source 9 on the basis of the current light emission pattern of the surface light source 9, and at least one of a brightness, contrast, and the relationship between the number of pixels and the luminance of an image acquired by the imaging optical system 11 with the light emission pattern.

The operation of the observation device 1 configured as described above will be described below.

Figure 2:
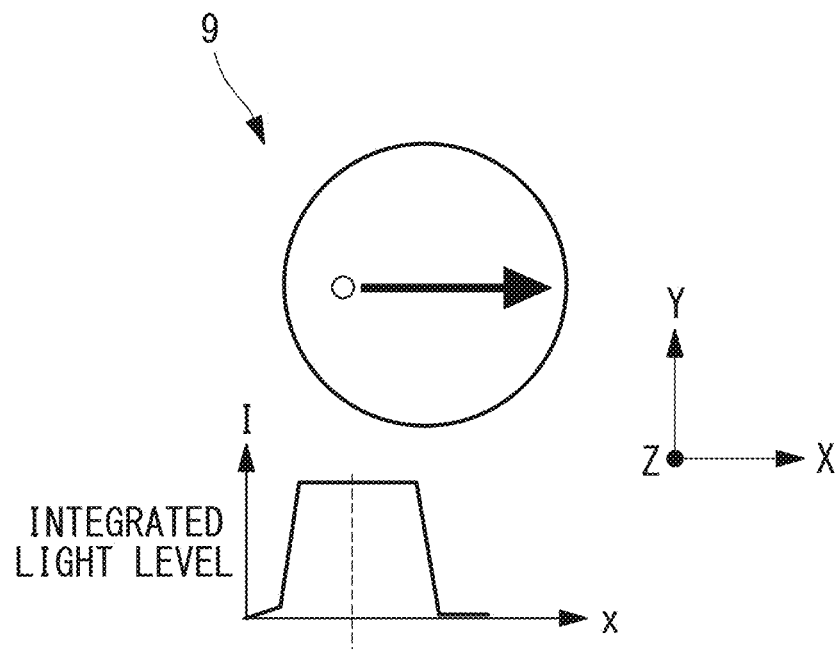
FIG. 2 is a diagram illustrating an example of a light emission pattern of a surface light source and an example of an integrated light level of observation light corresponding to the light emission pattern.

In order to observe the specimen S with the observation device 1 according to the present embodiment, the specimen container 3 containing the specimen S is mounted on the stage 5, and, for example, as illustrated in FIG. 2, the recording and calculation device 13 causes one point on the surface light source 9 to emit light, and emits spot-like illumination light in a light emission pattern in which the position of one point of where light is to be emitted is shifted in the X direction.

The spot-like illumination light emitted from one point on the surface light source 9 is transmitted through the light separating portion 15 and collected by the objective lens 7, transmitted through the stage 5 and the bottom portion 3a of the specimen container 3, and is radiated onto the specimen S from below. After observation light, which has been reflected from the specimen S due to the specimen S being irradiated with the illumination light, has been transmitted through the bottom portion 3a of the specimen container 3 and the stage 5 and collected by the objective lens 7, the light is reflected by the light separating portion 15 and is captured on the imaging surface of the imaging element 19 by the imaging lens 17. Thereby, image information of the specimen S is acquired by the imaging element 19 and sent to the recording and calculation device 13.

Figure 3:
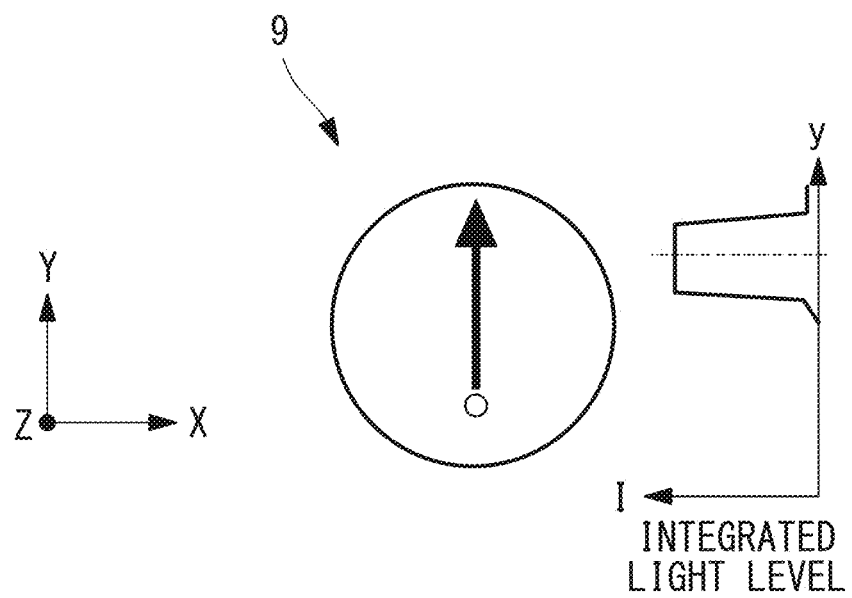
FIG. 3 is a diagram illustrating another example of a light emission pattern of a surface light source and an example of an integrated light level of observation light corresponding to the light emission pattern.

Next, as illustrated in FIG. 3, for example, the recording and calculation device 13 causes one point on the surface light source 9 to emit light, and emits spot-like illumination light in a light emission pattern in which the position of the one point where light is to be emitted is shifted in the Y direction.

The spot-like illumination light emitted from one point on the surface light source 9 passes through the stage 5 and the bottom portion 3a of the specimen container 3 via the light separating portion 15 and the objective lens 7, and irradiates the specimen S from below. Observation light reflected by the specimen S is transmitted through the bottom portion 3a of the specimen container 3 and the stage 5 and is captured on the imaging surface of the imaging element 19 by the imaging lens 17 via the objective lens 7 and the light separating portion 15. Then, image information of the specimen S acquired by the imaging element 19 is sent to the recording and calculation device 13.

Next, from a light amount distribution of observation light imaged by the imaging element 19 in a light emission pattern when one point on the surface light source 9 emits light as illustrated in FIG. 2 and a light amount distribution of observation light imaged by the imaging element 19 in the light emission pattern when one point on the surface light source 9 emits light as illustrated in FIG. 3, the recording and calculation unit 23 calculates pupil eccentricity on the basis of the current light emission position and the light emission range at which the respective light amount distributions are maximized. Then, on the basis of the calculated pupil eccentricity, the recording and calculation unit 23 adjusts the light emission pattern of the surface light source 9 so that the illumination light is emitted from a light emission position and a light emission range where the light amount distribution is maximum. Thus, a bright image of the specimen S can be acquired.

As described above, with the observation device 1 according to this embodiment, by performing illumination and image capturing below the specimen container 3 through the bottom portion 3a of the specimen container 3, an available specimen container does not have to have a side surface with a limited shape as in the configuration where illumination light is incident on the container from the side, and the apparatus can be reduced in size by not disposing the optical system above the specimen S.

In this case, a bright image of the specimen S can be acquired by the recording and calculation unit 23 correcting the light emission pattern of the illumination light from the surface light source 9 on the basis of the brightness of the image acquired by the imaging optical system 11 for the light emission pattern. Therefore, it is possible to deal with specimen containers 3 having various shapes, and to acquire a fine image of the specimen S in a small space such as an incubator.

Further, instead of shifting the spot-shaped illumination light emitted from one point on the surface light source 9 in the X direction and the Y direction, a method may be used in which a plurality of points continuous in either the X direction or the Y direction of the surface light source 9 are simultaneously emitted, and the positions of the plurality of points continuous in the X direction or the Y direction are shifted in the Y direction or the X direction.

Figure 4:
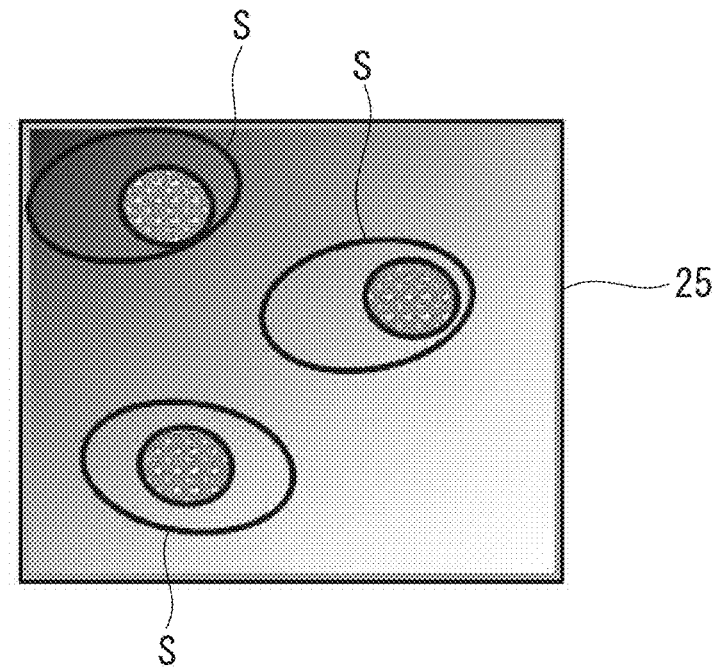
FIG. 4 is a diagram illustrating an example of an image having overexposed pixels and a completely dark region.
Figure 5:
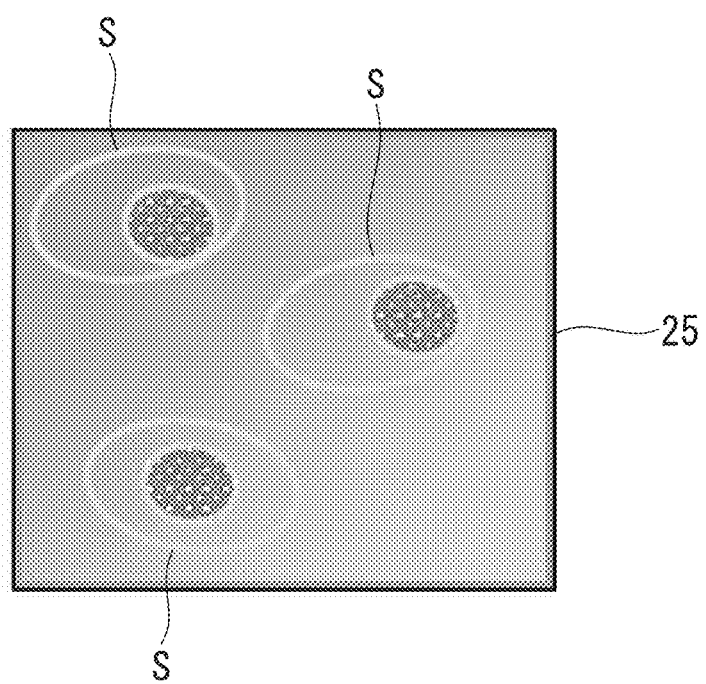
FIG. 5 is a diagram illustrating an example of an image with low contrast.

In addition, in the present embodiment, the recording and calculation unit 23, for example, may correct the light emission pattern of the surface light source 9 on the basis of the brightness of the image so that there are no overexposed pixels or dark regions in the image, as illustrated in FIG. 4, or alternatively may correct the light emission pattern of the surface light source 9 on the basis of the image contrast so that the contrast does not disappear, as illustrated in FIG. 5.

Figure 6:
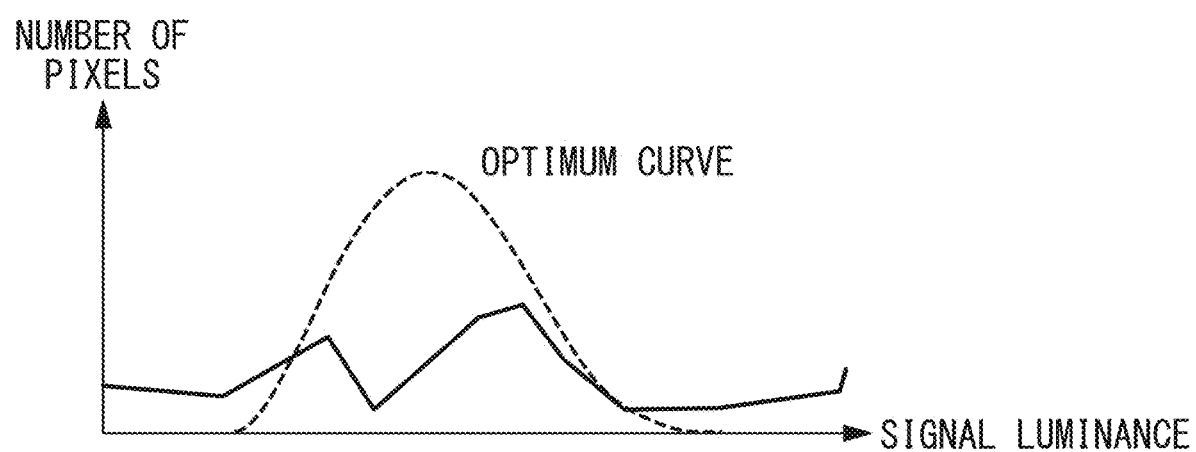
FIG. 6 is a histogram illustrating an example of the relationship between the number of pixels and signal luminance in an image in which overexposed pixels and dark regions are widely distributed.
Figure 7:
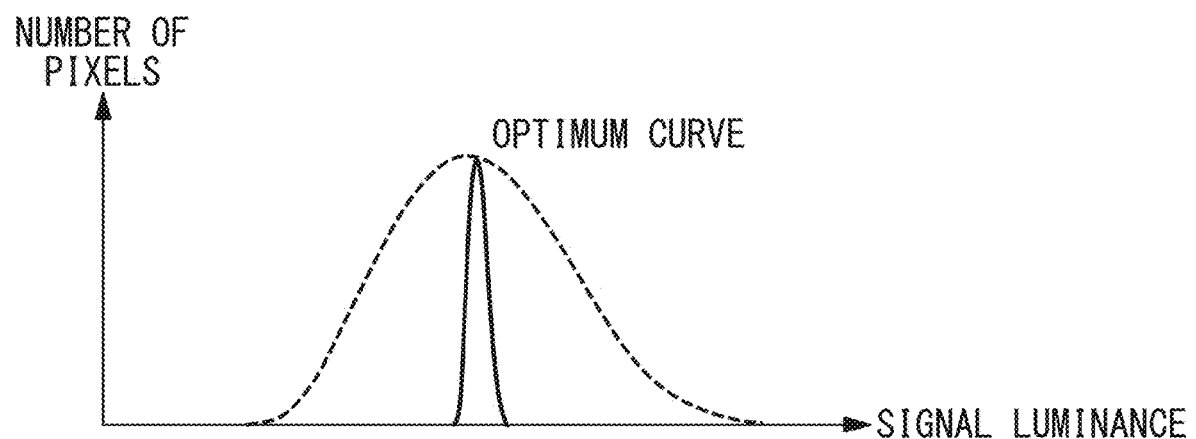
FIG. 7 is a histogram illustrating an example of the relationship between the number of pixels and the signal luminance in an image without contrast.

In addition, in the present embodiment, the recording and calculation unit 23 may correct the light emission pattern of the surface light source 9 on the basis of the relationship between the number of pixels of the image and the signal luminance of the image information, for example, on the basis of a histogram such as that illustrated in FIG. 6 or FIG. 7. The histogram illustrated in FIG. 6 illustrates that overexposed pixels and dark regions are widely distributed, and the histogram illustrated in FIG. 7 illustrates that there is no contrast. In either case, in FIGS. 6 and 7, the recording and calculation unit 23 may correct the light emission pattern of the surface light source 9 such that the relationship between the number of pixels and the signal luminance becomes an optimum curve.

This embodiment can be modified as follows.

Figure 8:
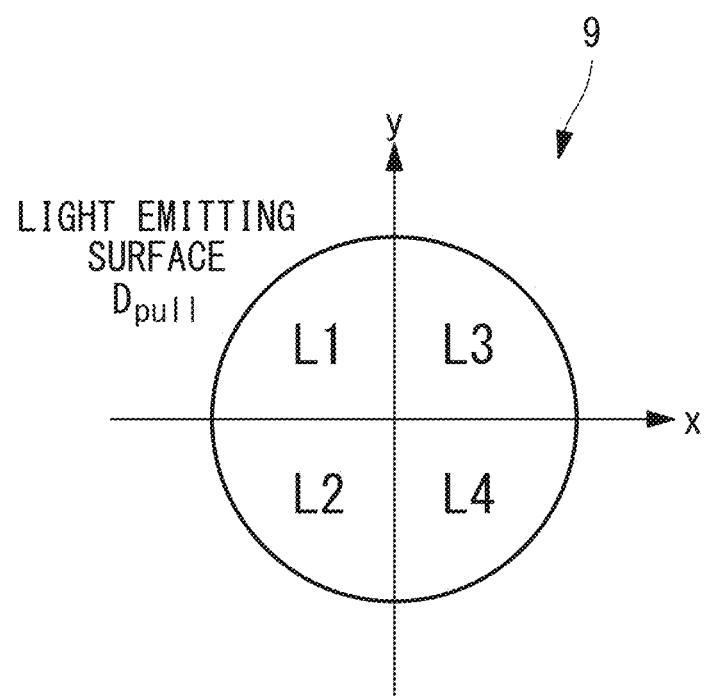
FIG. 8 is a plan view illustrating a light emitting surface of a surface light source obtained by dividing a light emitting region into four parts.

As a modification, as illustrated in FIG. 8, the light emission pattern of the surface light source 9 may be corrected such that the light emission position and the light emitting range of the surface light source 9 are divided into a plurality of regions, for example, four light emitting regions L1, L2, L3, and L4, the light emitting regions L1, L2, L3, and L4 are sequentially switched to emit light, and the center of gravity of one of the light-emitting regions L1, L2, L3, and L4 where the image acquired by the imaging optical system 11 is brightest is located at the center of the entire light-emitting region.

Figure 9:
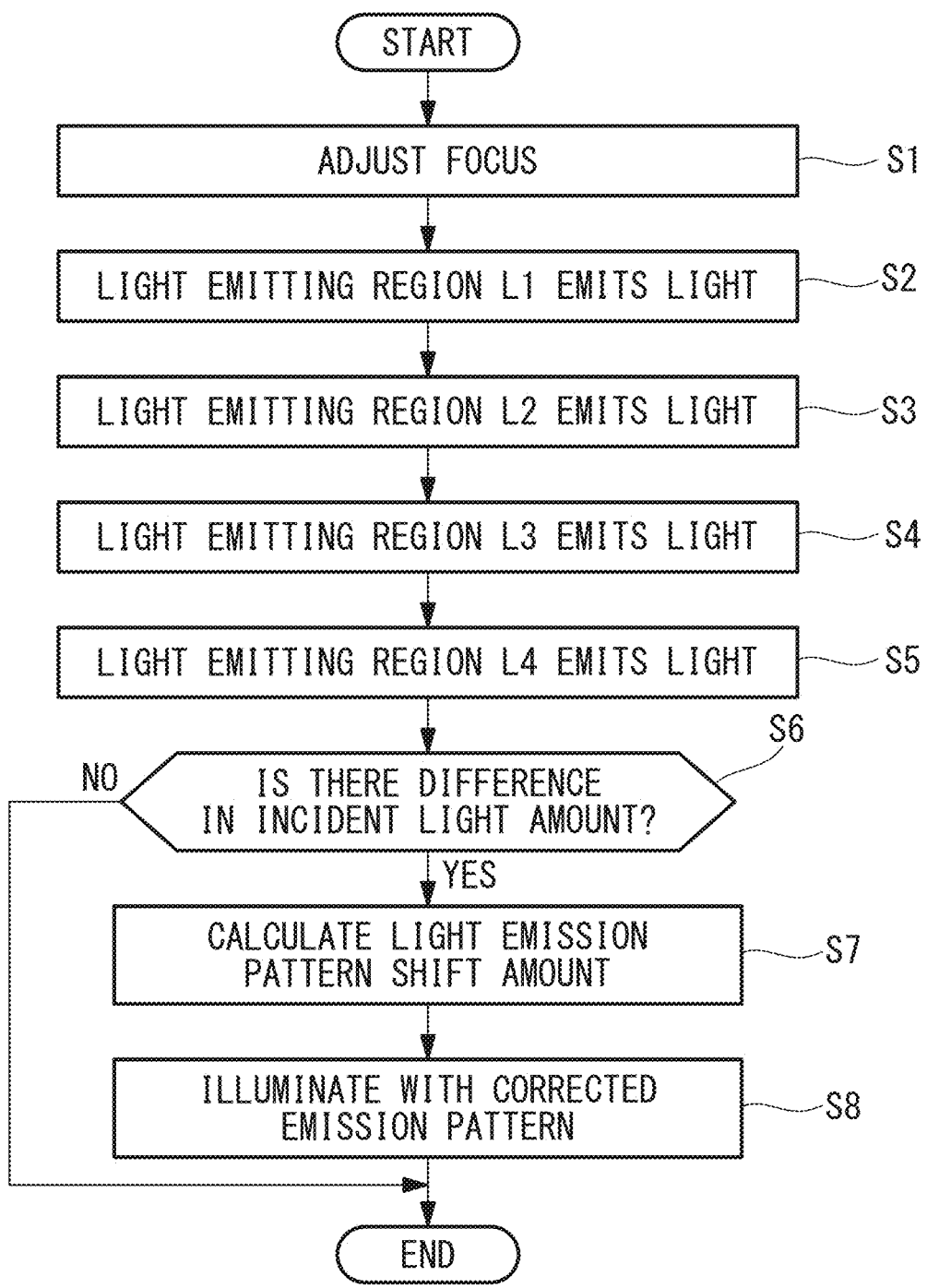
FIG. 9 is a flowchart illustrating steps in a case where a specimen is observed by an observation device according to a modification of the first embodiment of the present invention.

When observing the specimen S according to this modification, for example, as illustrated in the flowchart in FIG. 9, first, an entire circular region including the center of the surface light source 9 is made to emit light, and the focus is adjusted (step S1). Next, an arbitrary region of the circular shape is divided into, for example, four, the light emitting region L1 emits light, and image information of the specimen S is acquired (step S2). Next, the light emitting region L2 is caused to emit light instead of the light emitting region L1, and image information of the specimen S is acquired (step S3). Similarly, image information of the specimen S is acquired by causing the light emitting region L3 to emit light instead of the light emitting region L2 (step S4), and image information of the specimen S is acquired by causing the light emitting region L4 to emit light instead of the light emitting region L3 (step S5).

Next, the recording and calculation unit 23 determines whether or not there is a difference between the amounts of incident observation light on the imaging surface of the imaging element 19 corresponding to each of the light emitting regions L1, L2, L3, and L4 or the evaluation values (step S6). If there is no difference between the amounts of incident light or the evaluation values, since there is no difference between the light emitting regions L1, L2, L3, and L4, the recording and calculation unit 23 does not correct the light emission pattern of the region emitted in step S1, and the image acquired by the imaging element 19 is used as is. The evaluation value may be set such that the value increases as the amount of incident light increases.

Figure 10:
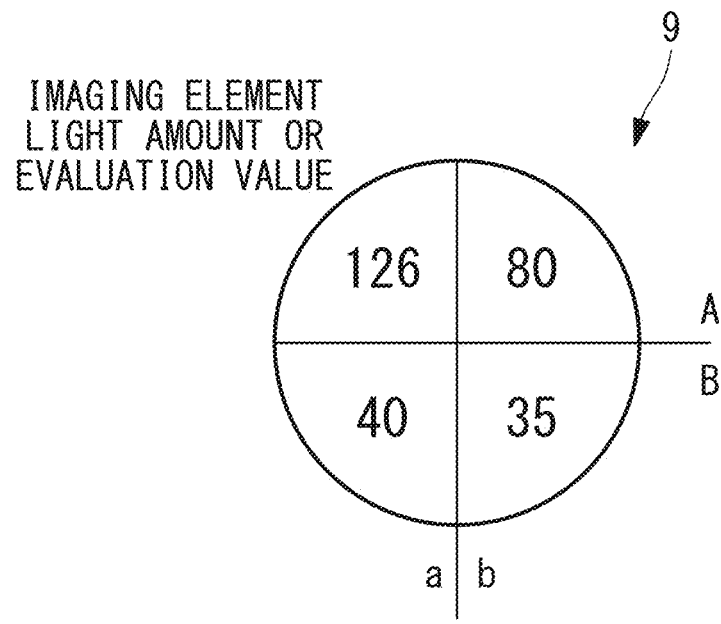
FIG. 10 is a diagram illustrating an example of an incident light amount or an evaluation value of observation light on an imaging surface of an imaging element corresponding to each light emitting region of a surface light source.

On the other hand, for example, as illustrated in FIG. 10, when there is a difference between the amounts of incident light, the recording and calculation unit 23 calculates a shift amount of the light emission pattern (step S7). In FIG. 10, the numerical values in each of the light emitting regions L1, L2, L3, and L4 indicate the incident light amounts or the evaluation values. For example, in the entire circular region of the surface light source 9, the light emitting regions L1 and L2 are a, the light emitting regions L3 and L4 are b, the light emitting regions L1 and L3 are A, and the light emitting regions L2 and L4 are B. In addition, the entire diameter of an arbitrary light emitting region in the surface light source 9 is Dpull.

In this case, the recording and calculation unit 23 calculates a shift amount Δx in the X direction by using the following equation (1).

$$\Delta x = \left(\frac{b}{a+b} - 0.5\right) \times D_{pull} \quad (1)$$

Further, a shift amount Δy in the Y direction is calculated by the following equation (2)

$$\Delta y = \left(\frac{A}{A+B} - 0.5\right) \times D_{pull} \quad (2)$$

Figure 11:
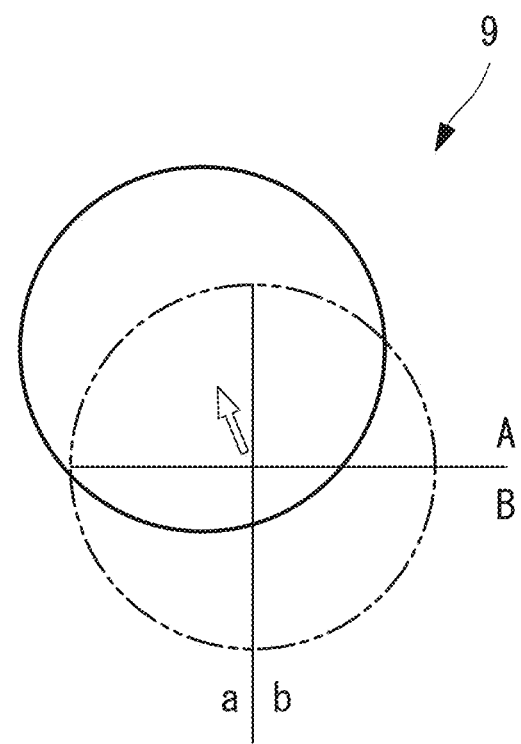
FIG. 11 is a plan view illustrating how the light emitting region of the surface light source is shifted.

For example, when Dpull=4 mm, the shift amount in the X direction is Δx=−0.363 mm, and the shift amount in the Y direction is Δy=0.96 mm. In this case, as illustrated in FIG. 11, the light emission pattern is corrected by the recording and calculation unit 23 so that the entire light emitting region of the surface light source 9 is moved to the light emitting region L1 side by Δx and Δy. Then, illumination is performed with the corrected light emission pattern to acquire an image of the specimen S (step S8).

According to the present modification, by changing the light emission pattern of the surface light source 9 and changing the illumination angle with respect to the specimen S, since the way in which shadows are cast on the specimen S changes and the brightness of the acquired image information changes, it is easy to see at which angle the illumination light is optimally irradiated. By shifting the light emitting region of the surface light source 9 in a direction in which bright image information can be acquired, a brighter image can be acquired. This is particularly effective when the number of specimens S is small at the initial stage of culturing specimens S such as cells or when it is desired to know the number of specimens S. In the present modification, the light emitting region is divided into four, but the number of divisions is not limited to this.

Figure 12:
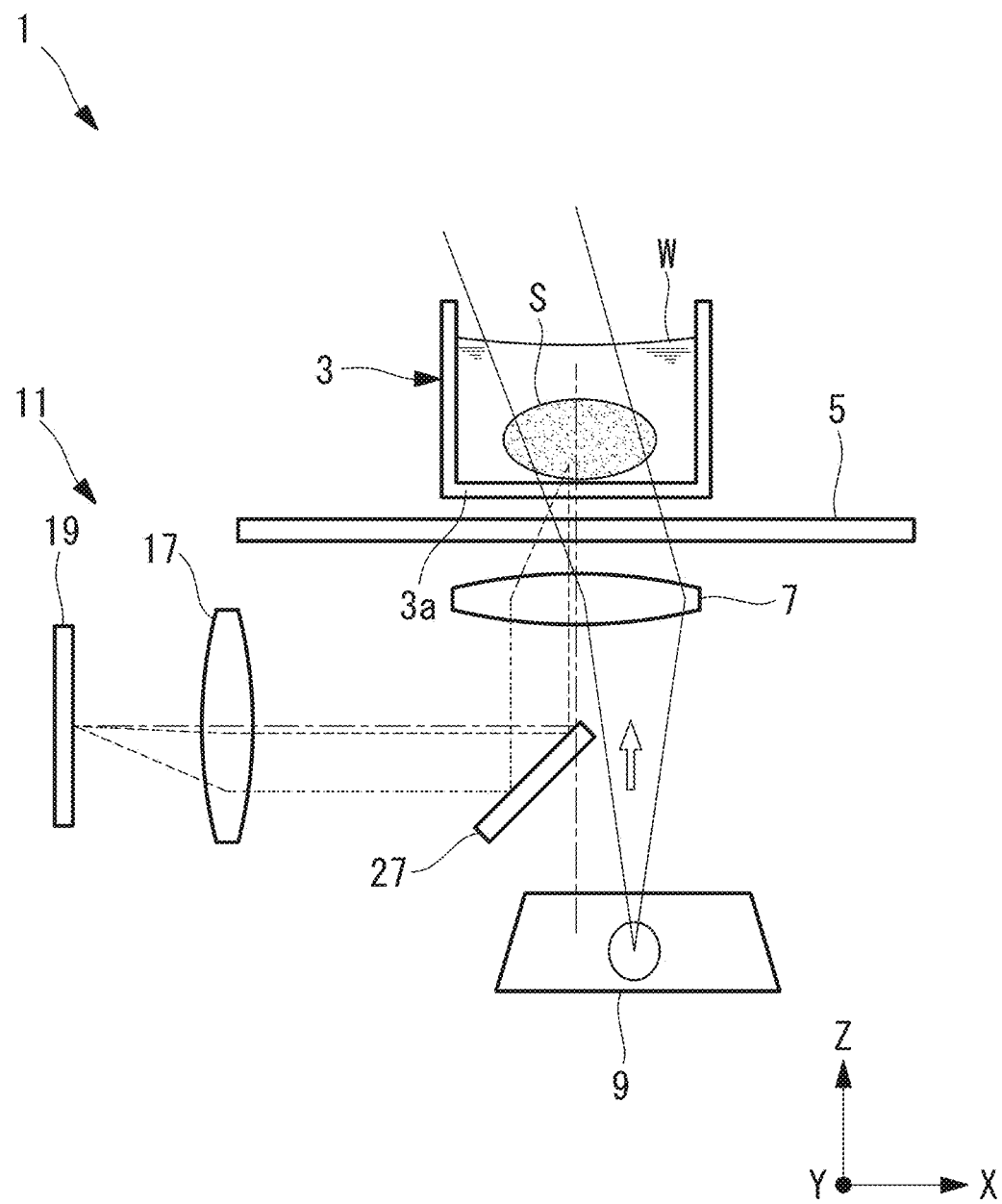
FIG. 12 is an overall configuration diagram of the case where a mirror is employed in place of the light separating portion in the observation device in FIG. 1.

In the above-mentioned modification, for example, as illustrated in FIG. 12, a mirror 27 may be employed in place of the light separating portion 15, illumination light emitted from the surface light source 9 may be made directly incident on the objective lens 7 to irradiate the specimen S from below the specimen container 3, and the observation light from the target S collected by the objective lens 7 may be reflected by the mirror 27 and made incident on the imaging lens 17.

Figure 13:
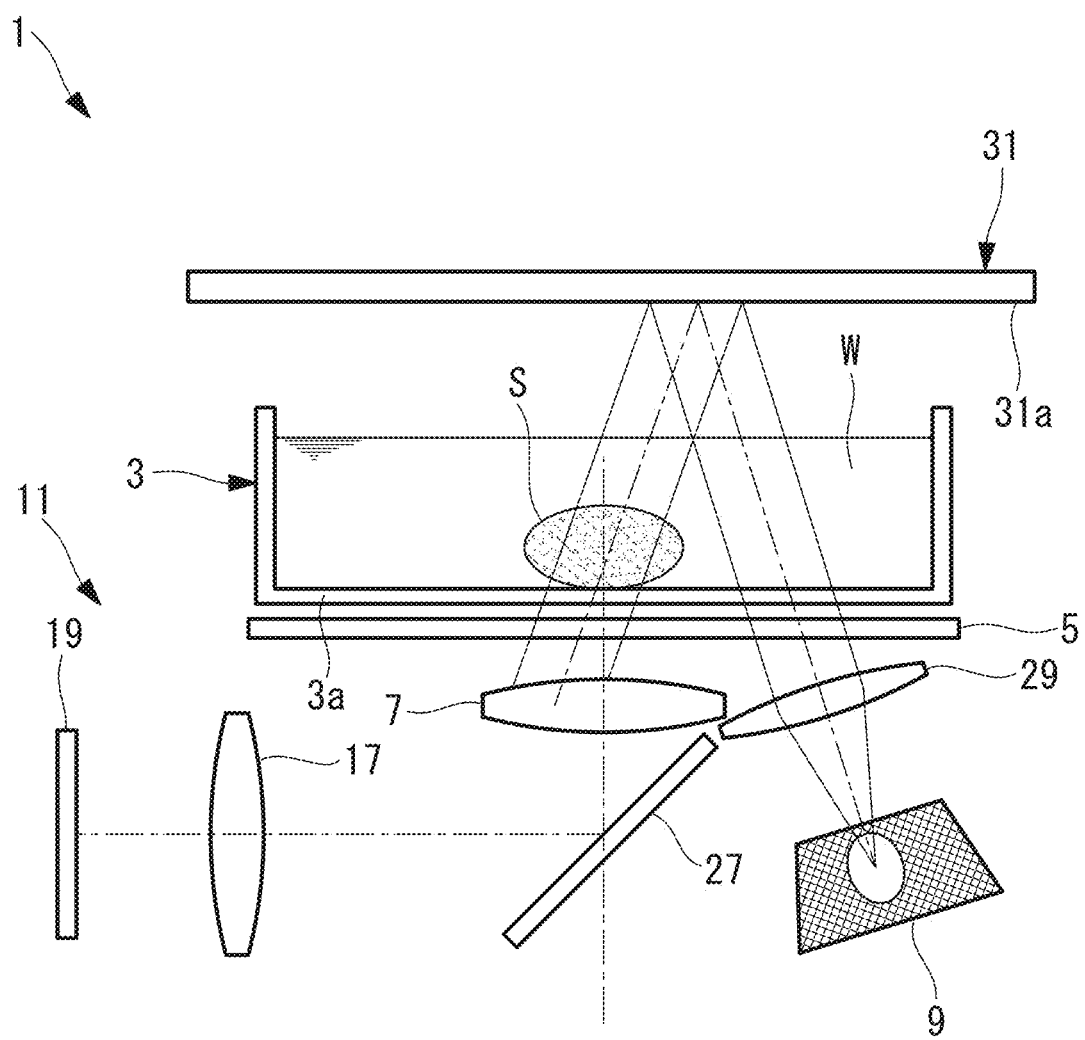
FIG. 13 is an overall configuration diagram in the case where the observation device in FIG. 12 further includes a condenser lens and a reflecting member.
Figure 14:
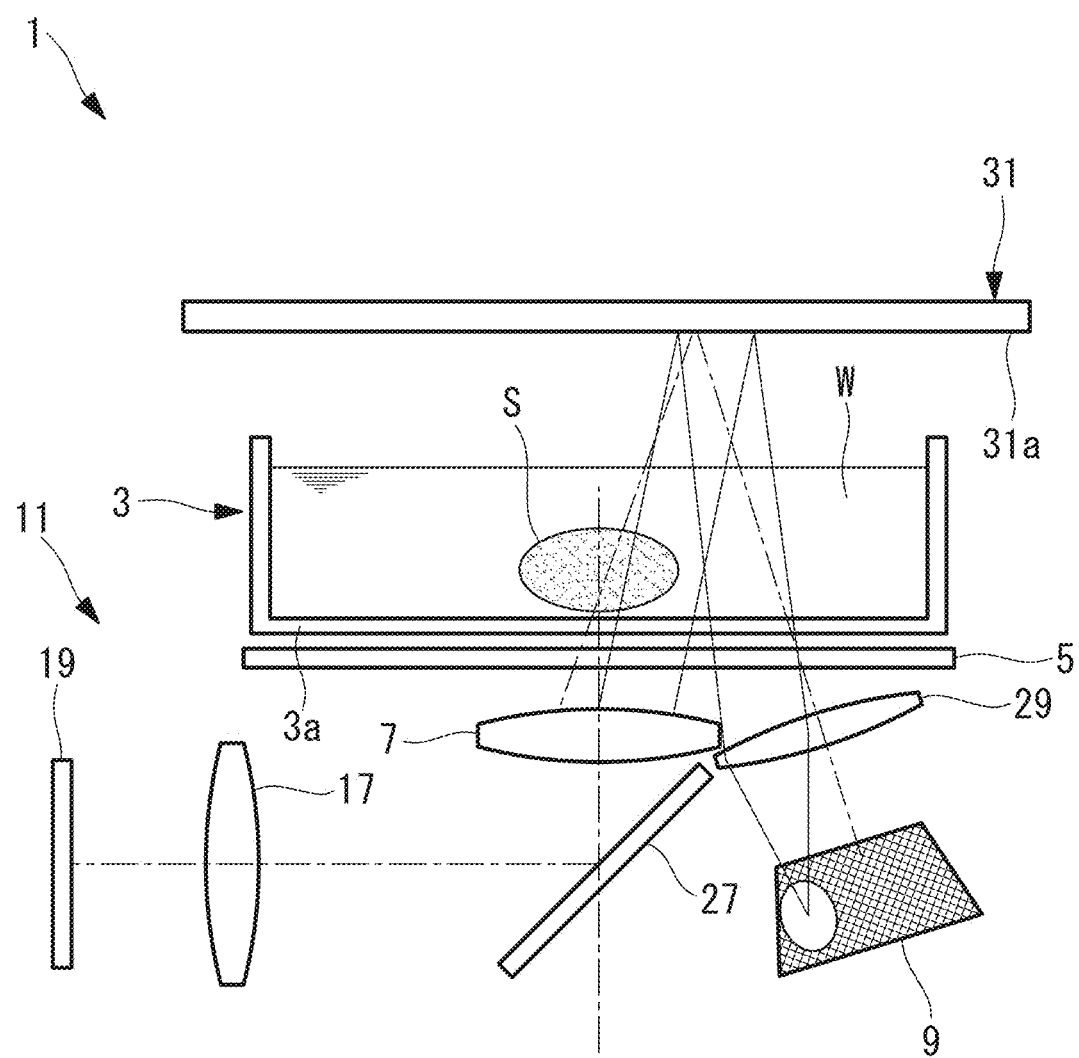
FIG. 14 is a diagram illustrating an example of an optical path of illumination light in a case where the light emitting region of the surface light source is changed in the observation device in FIG. 13.

In addition, as illustrated in FIGS. 13 and 14, a condenser lens 29 that focuses the illumination light emitted from the surface light source 9 and makes it enter the specimen container 3 from the bottom portion 3a without passing through the objective lens 7, and a reflecting member 31 disposed above the specimen S and having a reflecting surface 31a that reflects the illumination light made incident on the specimen container 3 by the condenser lens 29 toward the specimen S may be included.

As the reflecting member 31, for example, a mirror or a lid of the specimen container 3 is used.

In this case, the condenser lens 29 and the surface light source 9 may be disposed with their positions shifted in the radial direction with respect to the optical axis of the objective lens 7 disposed vertically below the specimen S, the illumination light may be emitted from the surface light source 9 toward the upper side of the specimen S via the condenser lens 29, the stage 5, and the bottom portion 3a of the specimen container 3, and the light may be reflected by the reflecting member 31 above the specimen S and may be made incident on the specimen S from obliquely above the optical axis of the objective lens 7. Then, the imaging optical system 11 may capture the observation light transmitted through the specimen S below the specimen S. The surface light source 9 may be disposed near a position conjugate with the pupil position in the optical path of the illumination light of the objective lens 7.

In this manner, by appropriately setting the angle of incidence of the illumination light on the specimen S, bright and dark regions are formed in the image of the specimen S, and an image that is easy to see even in the case of a transparent subject such as a cell can be acquired. In addition, it is possible to perform transmission illumination only by disposing the reflecting member 31 without disposing a light source above the specimen container 3. Consequently, it is possible to secure a space above the specimen S, and to easily observe a specimen S such as a transparent cell.

Second Embodiment

Next, an observation device according to the second embodiment of the present invention will be described.

Figure 15:
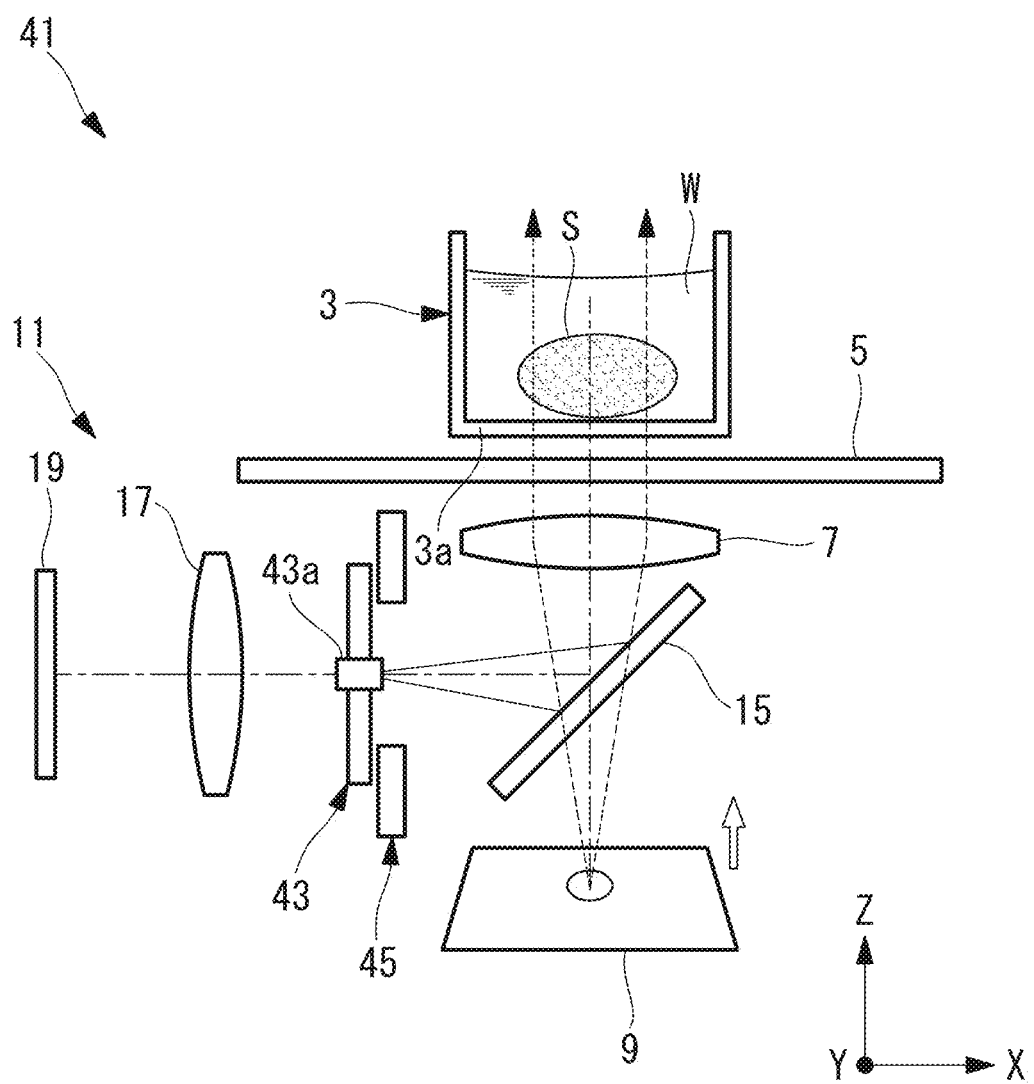
FIG. 15 is an overall configuration diagram illustrating an observation device according to a second embodiment of the present invention.

As illustrated in FIG. 15, an observation device 41 according to the present embodiment includes a light-blocking film (dimming member, phase modulation element) 43 disposed at a pupil position of the objective lens 7 in an optical path of the imaging optical system 11, and the second embodiment differs from the first embodiment in that the specimen S is subjected to incident dark-field observation.

Hereinafter, portions having the same configuration as the observation device 1 according to the first embodiment are denoted by the same reference numerals, and the description thereof is omitted.

(4) The light-blocking film 43 has a disk shape in which a light-blocking portion 43a for blocking light is formed at the center. This light-blocking film 43 has a conjugate positional relationship with the surface light source 9, and is arranged such that the light-blocking portion 43a is located on the optical axis of the imaging lens 17. Thereby, zero-order light of the observation light from the specimen S incident on the light-blocking portion 43a is blocked. An aperture 45 is disposed in front of the light-blocking film 43.

The recording and calculation unit 23, by executing a program, corrects the light emission pattern of the surface light source 9 on the basis of the current light emission pattern of the surface light source 9 and at least one of the brightness, contrast, and the relationship between the number of pixels and the luminance of an image acquired by the imaging optical system 11 with the light emission pattern, such that the observation light from the specimen S focused by the objective lens 7 is incident on the light-blocking film 43.

The operation of the observation device 41 configured as described above will be described.

When observing the specimen S with the observation device 41 according to the present embodiment, within the observation light from the specimen S, the zero-order light is blocked by the light-blocking portion 43a of the light-blocking film 43, and the refracted or reflected light is imaged by the imaging lens 17 on the imaging surface of the imaging element 19. Consequently, dark field observation of the specimen S can be performed.

Figure 16:
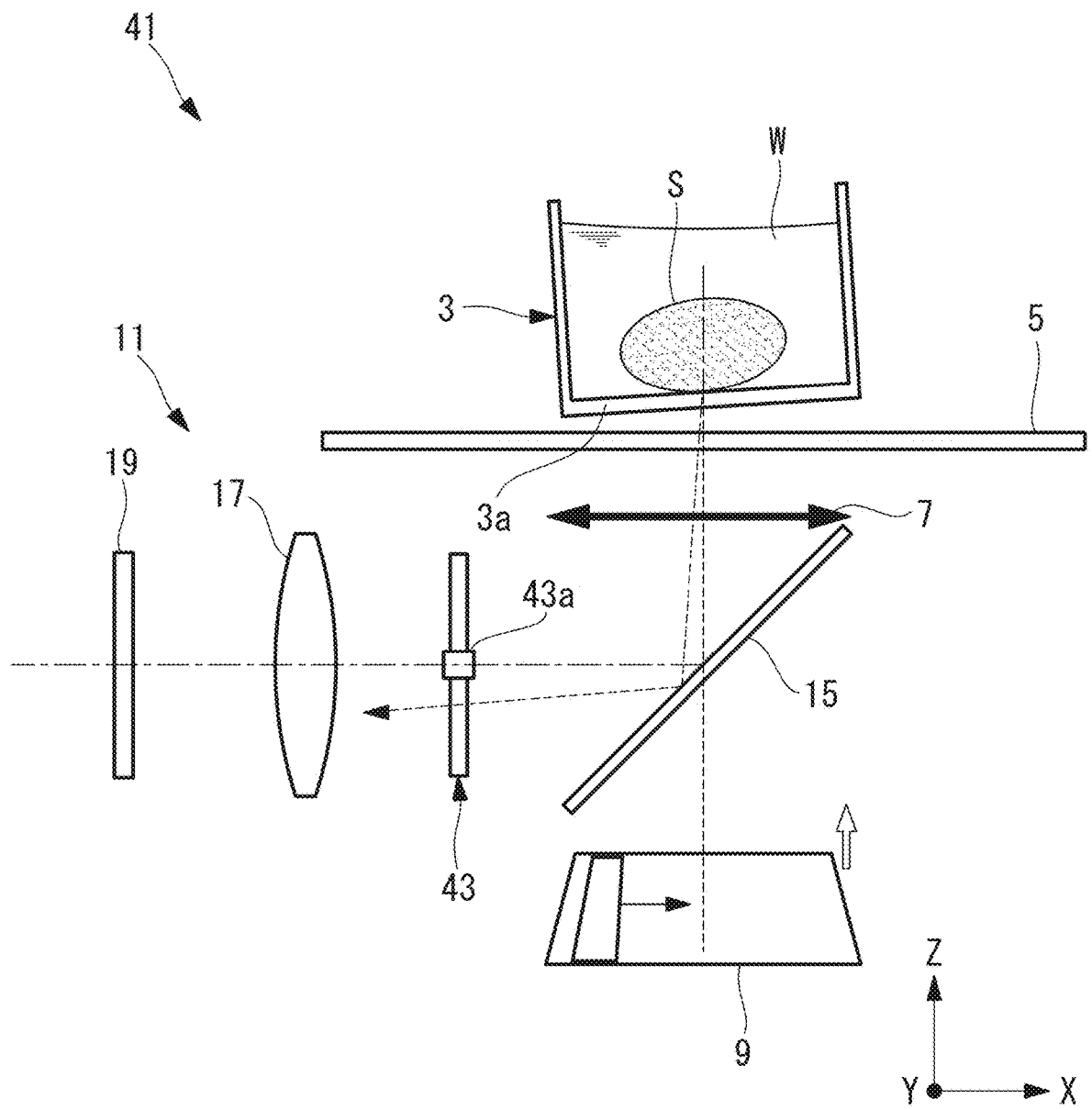
FIG. 16 is a diagram illustrating an example of an optical path of observation light when a bottom portion of a specimen container is inclined in the observation device in FIG. 15.

In this case, for example, as illustrated in FIG. 16, when the bottom portion 3a of the specimen container 3 is inclined, the bottom portion 3a is warped, or the bottom portion 3a has a wedge shape, the observation light from the specimen S is refracted at the bottom portion 3a of the specimen container 3 and the zero-order light does not enter the light-blocking portion 43a of the light-blocking film 43.

Figure 17:
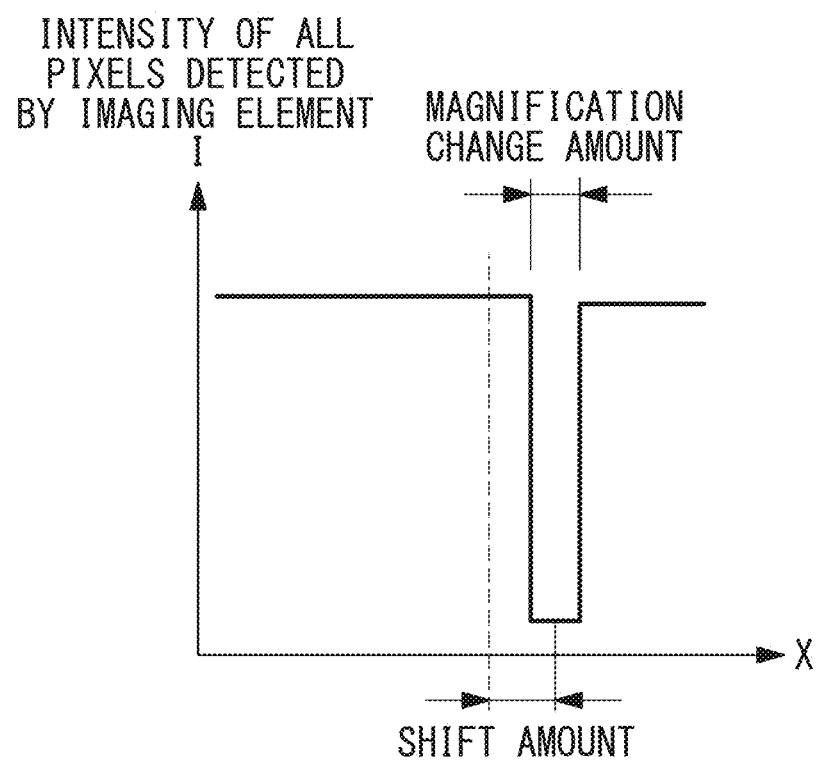
FIG. 17 is a diagram illustrating the relationship between the position of a light receiving pixel in the X direction of an imaging element and the intensity of all pixels detected by the imaging element.

Therefore, for example, a plurality of points continuous in the Y direction of the surface light source 9 are simultaneously emitted, and linear illumination light is emitted in a light emission pattern in which the positions of the plurality of consecutive points in the Y direction to be emitted are shifted in the X direction. Then, as illustrated in FIG. 17, at a certain position in the X direction, since the detection intensity of the imaging element 19 is reduced due to the observation light being blocked by the light-blocking portion 43a of the light-blocking film 43, the light emission position in the X direction of the surface light source 9 at which the zero-order light can be made incident on the light-blocking portion 43a of the light-blocking film 43 can be determined from the position where the detection intensity decreases. In FIG. 17, the horizontal axis indicates the position of the light receiving pixel in the X direction of the imaging element 19, and the Y axis indicates the intensity of all pixels detected by the imaging element 19.

In addition, in FIG. 17, the emission range of the surface light source 9 can be determined from the width in the X direction in which the detection intensity of the imaging element 19 is reduced. In this case, if the bottom portion 3a of the specimen container 3 is warped, the observation light is refracted at the bottom portion 3a, and the magnification of the observation light beam with respect to the illumination light beam changes.

Therefore, for example, the recording and calculation unit 23 corrects the light emission pattern of the surface light source 9 so as to reduce the width of the light emitting region of the surface light source 9 in the X direction if the width in the X direction where the detection intensity of the imaging element 19 is reduced is larger than the width of the light emitting region of the surface light source 9 in the X direction, and so as to increase the width of the light emitting region of the surface light source 9 in the X direction if the width in the X direction where the detection intensity of the imaging element 19 is reduced is smaller than the width of the light emitting region of the surface light source 9 in the X direction such that the width of the light emitting region of the surface light source 9 in the X direction and the width in the X direction (magnification change amount) where the detection intensity of the imaging element 19 is reduced are set to be 1:1.

Similarly, by emitting a plurality of points continuous in the X direction simultaneously from the surface light source 9, emitting a linear illumination light in a light emission pattern in which the positions of the plurality of points continuous in the X direction to be emitted are shifted in the Y direction, and specifying the position where the detection intensity of the imaging element 19 decreases and the magnification change amount, the light emission position of the surface light source 9 in the Y direction and the correction amount of the light emitting range are determined.

Therefore, by correcting the light emission position and the light emission range of the surface light source 9 in the X and Y directions by the recording and calculation unit 23, the zero-order light of the observation light is blocked by the light-blocking portion 43a of the light-blocking film 43, and the specimen S can be observed with high definition in a dark field.

This embodiment can be modified as follows.

Figure 18:
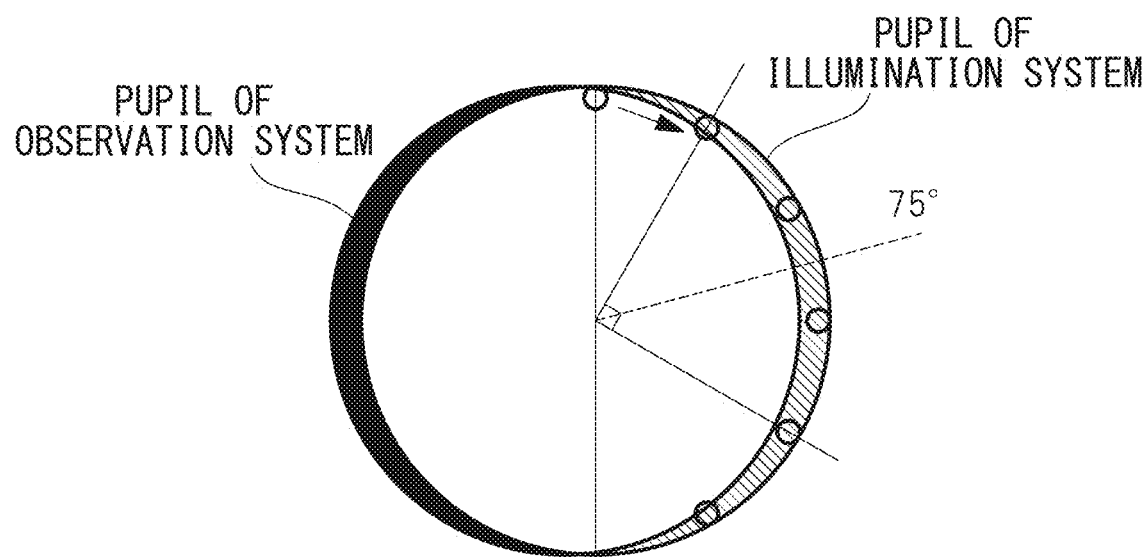
FIG. 18 is a plan view illustrating a state in which an incident position of illumination light on a pupil of an objective lens is switched.
Figure 19:
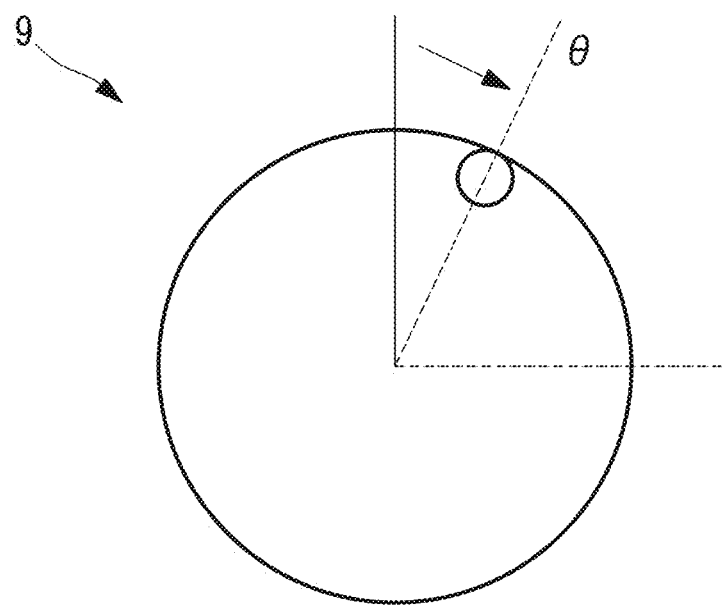
FIG. 19 is a plan view illustrating a state in which the light emission pattern of the surface light source is switched in a circumferential direction.
Figure 20:
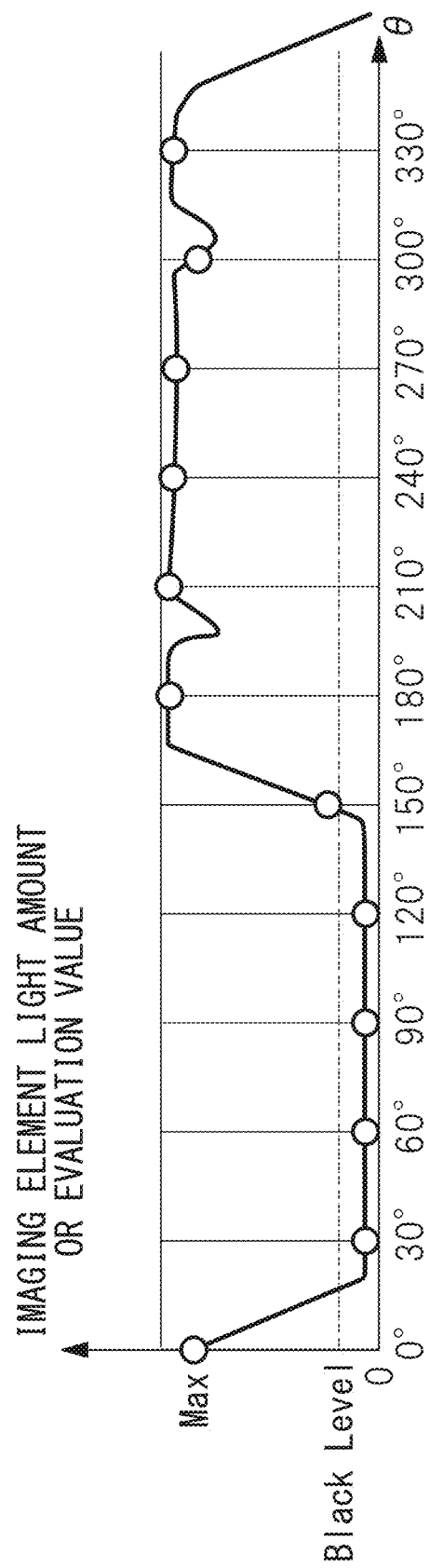
FIG. 20 is a diagram illustrating an example of the relationship between the angle of a light emission position around a center axis and an incident light amount or an evaluation value when the light emission position of a surface light source is divided into twelve in the circumferential direction and switched.

For example, as illustrated in FIG. 19, the light emission position on the surface light source 9 may be switched in the circumferential direction such that spot-like illumination light is sequentially incident on the inside of the pupil of the objective lens 7 along the outer periphery thereof, as illustrated in FIG. 18. FIG. 20 illustrates the relationship between the angle of the light emission position around the center axis and the amount of incident light or the evaluation value of the imaging element 19 when the light emission position of the surface light source 9 is divided into 12 in the circumferential direction and switched. In FIG. 18, ○ indicates the incident position of the illumination light on the pupil of the objective lens 7, and in FIG. 19, ○ indicates the light emission position on the surface light source 9.

In the example illustrated in FIG. 20, because the amount of incident light or the evaluation value of the imaging element 19 decreases when light is emitted from the light emission position where the angle around the center axis is 30°, 60°, 90°, or 120°, it can be understood that the observation light from the specimen S is blocked by the aperture 45 when the illumination light from those positions is radiated.

For example, in the example illustrated in FIG. 21, when the upper limit (black level) for determining darkness is set to a light amount 10, the light amount is 10 or less at the light emission positions S2 to S5, and the blocked range is θ=30° to 120°, and the angle of the blocked direction is (120−30)/2+30=75°. In addition, because there are four light emission positions at the black level or less when the pupil diameter is φ4 and the light source size on the pupil is φ0.1, the shift amount (eccentric amount) is 0.155 mm from FIG. 22. In FIG. 22, BLn indicates the number of light emission positions at which the light emission level is equal to the black level or less.

Figure 23:
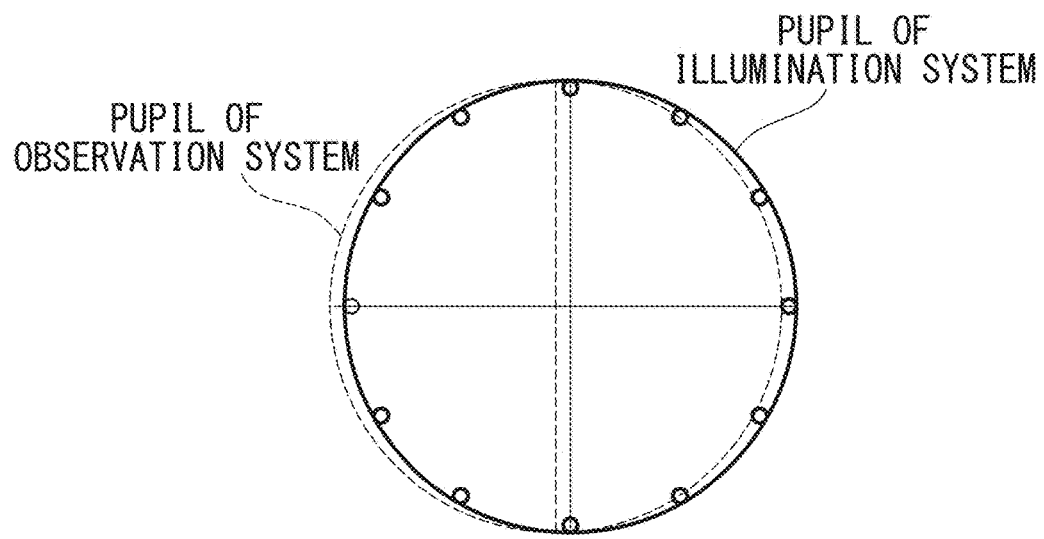
FIG. 23 is a diagram illustrating an example of an incident position of illumination light on a pupil of an objective lens when there are no light-emission positions at the black level or less.
Figure 24:
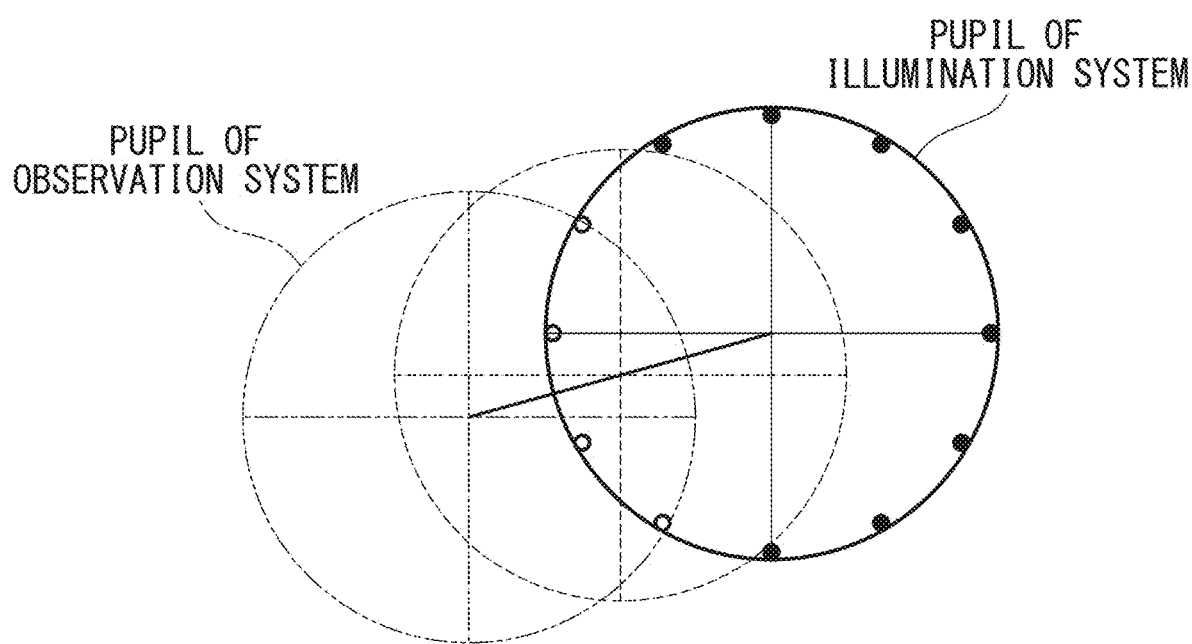
FIG. 24 is a diagram illustrating an example of the incident position of illumination light on the pupil of the objective lens when the number of light emission positions at the black level or less is eight or more.

Further, as illustrated in FIG. 23, when there are no light emission positions at the black level or less, the recording and calculation unit 23 does not correct the light emission pattern of the surface light source 9 and may use the image acquired by the imaging element 19 as is. On the other hand, as illustrated in FIG. 24, the shift amount cannot be specified when the number of light emission positions at the black level or less is eight or more. In FIGS. 23 and 24, ○ indicates an incident position where the amount of light at the pupil of the objective lens 7 is larger than the black level, and ● indicates an incident position where the amount of light at the pupil of the objective lens 7 is the black level or less.

Figure 25:
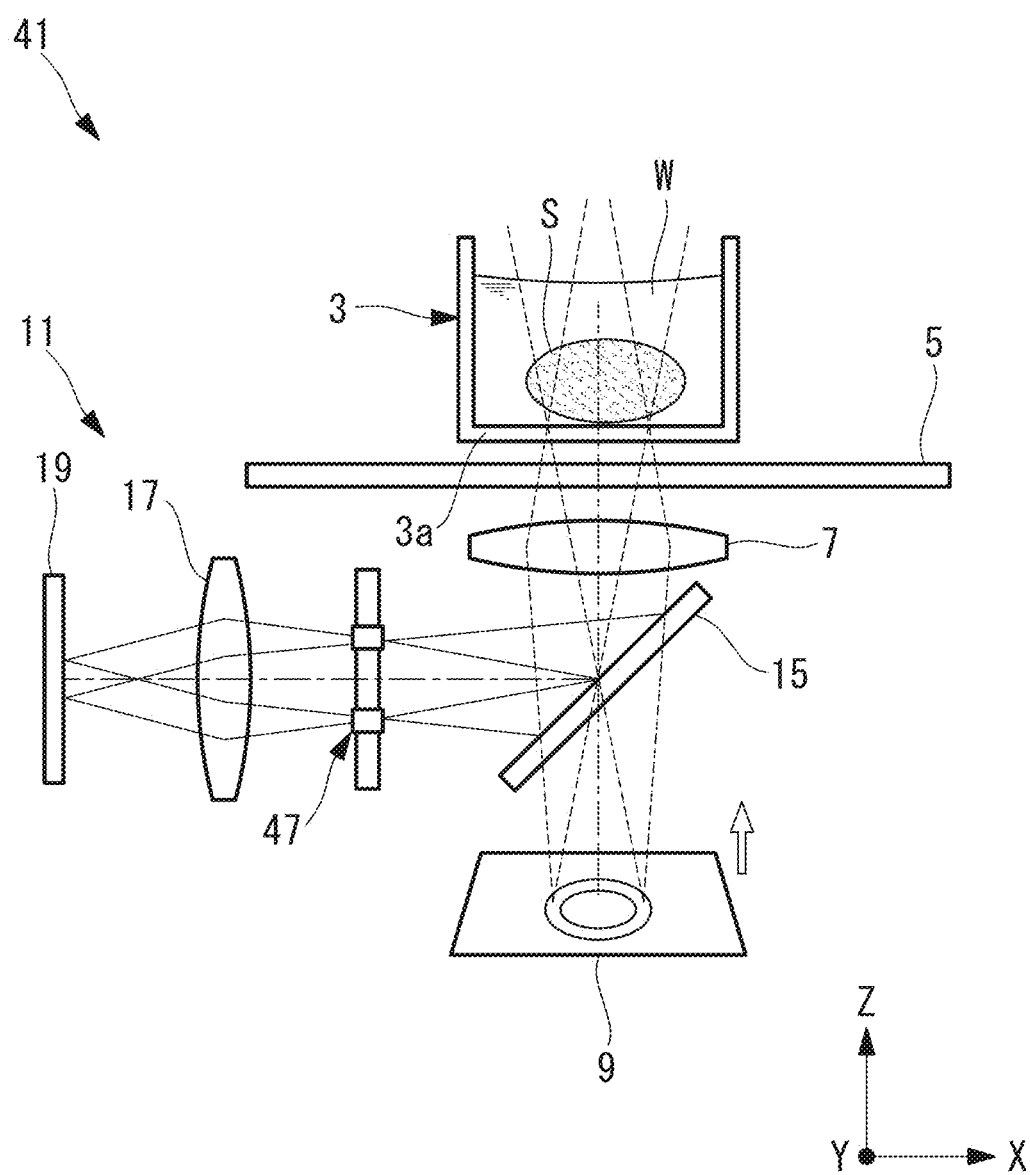
FIG. 25 is an overall configuration diagram in the case where a phase film is employed as a phase modulation element in the observation device in FIG. 15.

In the present embodiment, the light-blocking film 43 has been described as an example of the phase modulation element; however, instead, for example, as illustrated in FIG. 25, a phase film 47 for phase-modulating the observation light may be employed. The phase film 47 illustrated in FIG. 25 is formed, for example, in a ring shape having a width in the radial direction.

In this case as well, a light emission position and a light emitting region of the surface light source 9 such that the observation light passes through the phase film 47 may be determined by the recording and calculation unit 23, and the light emission pattern of the surface light source 9 may be corrected so that the light is emitted at the light emission position and the light emission region. In this case, direct light from the specimen S passing through the phase film 47 and diffracted light not passing through the phase film 47 are focused by the imaging lens 17, and an image having a bright and dark contrast on the imaging surface of the imaging element 19 is formed. Consequently, the specimen S can be observed with a high-definition phase difference.

Third Embodiment

Next, an observation device according to a third embodiment of the present invention will be described.

Figure 26:
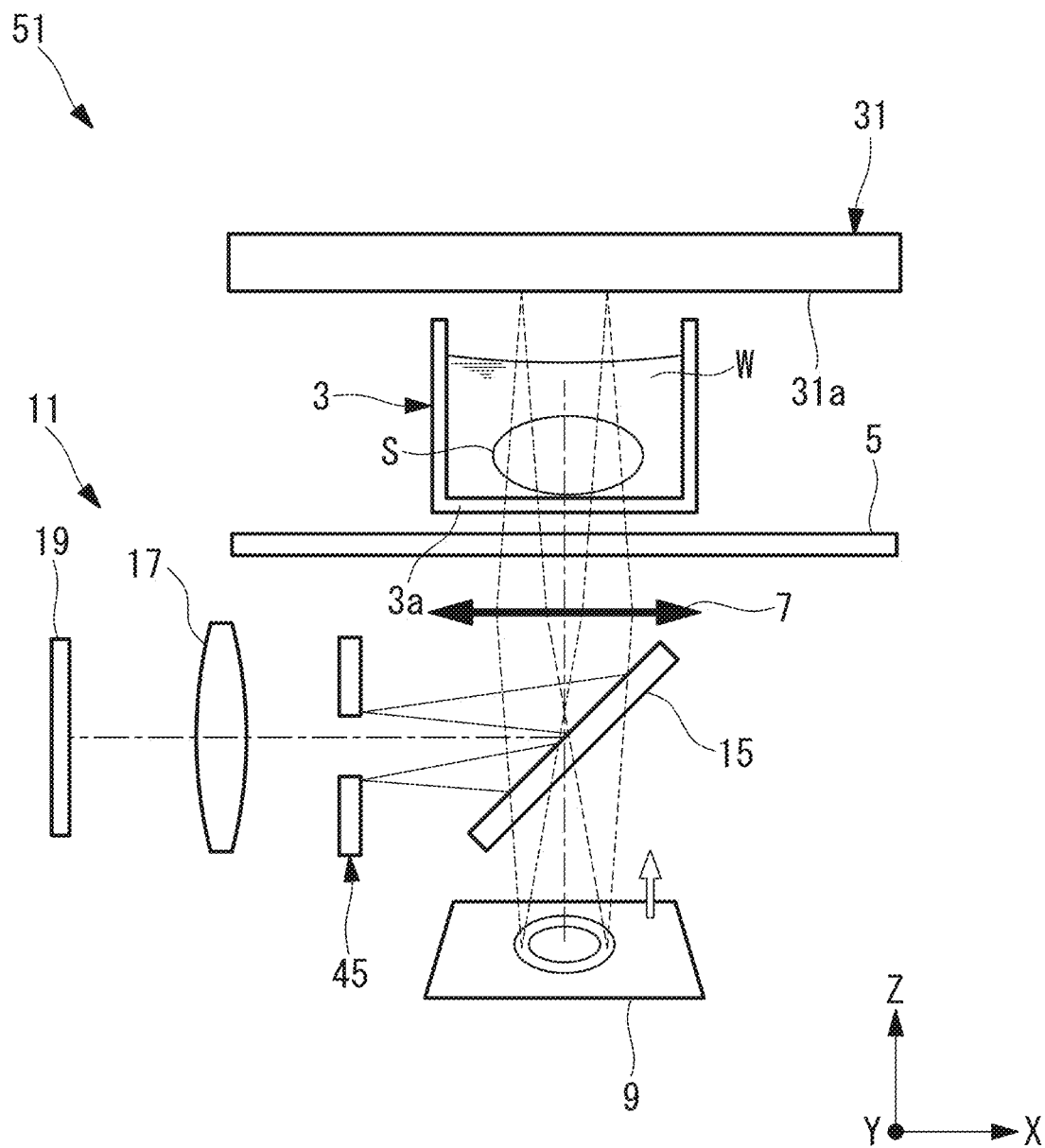
FIG. 26 is an overall configuration diagram illustrating an observation device according to a third embodiment of the present invention.

The third embodiment differs from the first embodiment and the second embodiment in that, as illustrated in FIG. 26, an observation device 51 according to the present embodiment includes the reflecting member 31 that is disposed above the specimen S and that reflects illumination light from the surface light source 9 toward the specimen, and the aperture (dimming member, phase modulation element) 45 arranged at the pupil position in the optical path of the imaging optical system 11 of the objective lens 7.

Hereinafter, portions having the same configuration as the observation devices 1 and 41 according to the first and second embodiments are denoted by the same reference signs, and the description thereof is omitted. In the example illustrated in FIG. 26, the observation device 51 includes a half mirror or a polarizing beam splitter serving as the light separating portion 15.

In the present embodiment, the recording and calculation unit 23, by executing a program, corrects the light emission pattern of the surface light source 9 on the basis of the current light emission pattern of the surface light source 9 and at least one of the brightness, contrast, and the relationship between the number of pixels and the luminance of an image acquired by the imaging optical system 11 with the light emission pattern, such that the observation light from the specimen S focused by the objective lens 7 passes through the aperture 45.

The operation of the observation device 51 thus configured will be described.

After the illumination light emitted from the surface light source 9 has been transmitted through the light separating portion 15, collected by the objective lens 7, and transmitted through the stage 5 and the bottom portion 3a of the specimen container 3, the illumination light is reflected by the reflecting surface 31a of the reflecting member 31 and irradiates the specimen S obliquely from above.

Then, the observation light of the illumination light transmitted through the specimen S passes through the bottom portion 3a of the specimen container 3 and the stage 5 from above to below, is collected by the objective lens 7, and is reflected by the light separating portion 15. Of the observation light reflected by the light separating portion 15, the light that has passed through the aperture 45 is imaged on the imaging surface of the imaging element 19 by the imaging lens 17.

At this time, the illumination light is refracted and scattered by the shape and refractive index of the specimen S, or dimmed by the transmittance of the specimen S, and observation light carrying information on the specimen S is collected by the objective lens 7 and imaged by the imaging element 19. Therefore, by appropriately setting the angle of incidence on the specimen S, it is possible to form bright and dark regions in the image of the specimen S, and it is possible to acquire an image that is easy to see even in the case of a transparent subject such as a cell.

In this case, through correction of the light emission pattern of the surface light source 9 by the recording and calculation unit 23 so that the observation light from the specimen S is reflected by the light separating portion 15 and passes through the aperture 45, it is possible to perform oblique illumination observation with high definition. In addition, a space can be secured above the specimen S, so that a specimen S such as a transparent cell can be easily observed.

This embodiment can be modified as follows.

Figure 27:
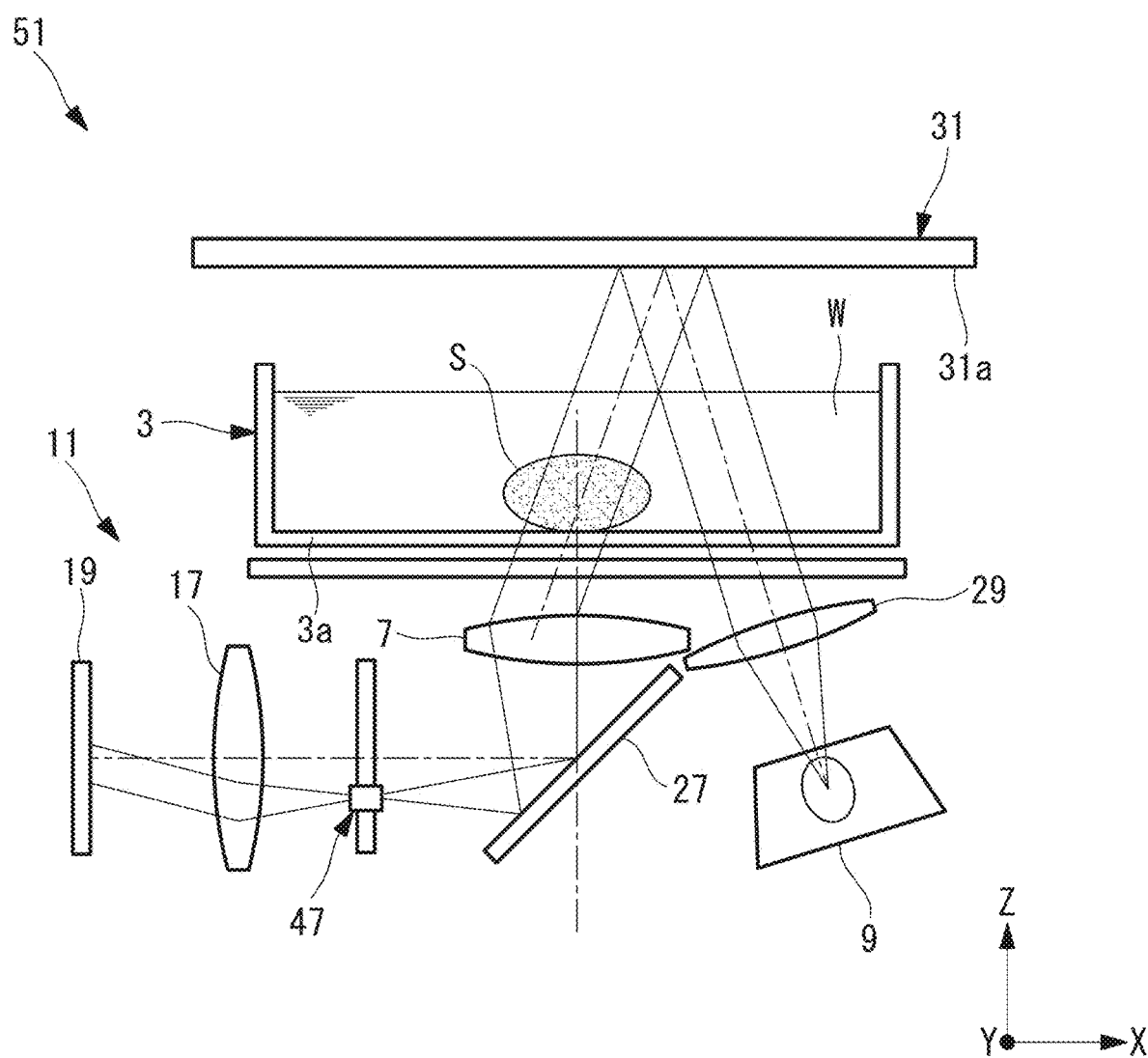
FIG. 27 is an overall configuration diagram in the case where the observation device in FIG. 26 further includes a condenser lens.

For example, as illustrated in FIG. 27, the condenser lens 29 that focuses illumination light emitted from the surface light source 9 and that allows the illumination light to enter the specimen container 3 from the bottom portion 3a without passing through the objective lens 7 may be provided, and the surface light source 9 and the condenser lens 29 may be disposed so as to be shifted from each other in the radial direction with respect to the optical axis of the objective lens 7. In this modification, the surface light source 9 may be disposed near a position conjugate with the pupil position in the optical path of the illumination light of the objective lens 7. In FIG. 27, the phase film 47 is employed as a phase modulation element.

In this case, the recording and calculation unit 23 may correct the emission pattern of the surface light source 9 so that the observation light from the specimen S is reflected by the mirror 27 and passes through the phase film 47.

In this manner, by appropriately setting the angle of incidence on the specimen S, the image of the specimen S can be made bright and dark, and it is possible to acquire an image that is easy to see even in the case of a transparent specimen S such as a cell. In addition, the phase difference can be observed by transmission illumination only by disposing the reflecting member 31 without disposing the light source above the specimen container 3. Consequently, it is possible to secure a space above the specimen S, and to easily observe the specimen S such as a transparent cell.

Figure 28:
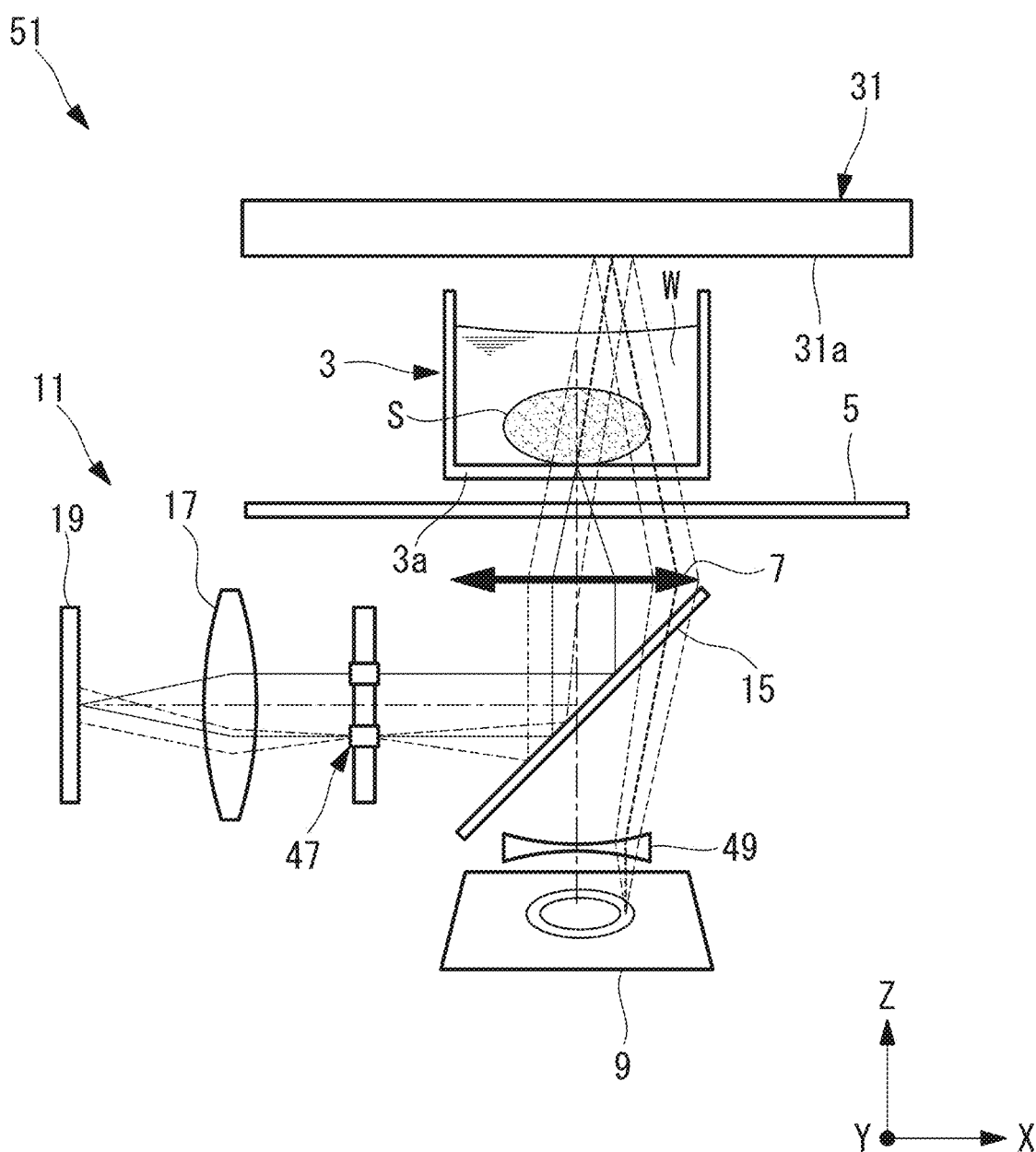
FIG. 28 is an overall configuration diagram in the case where the observation device in FIG. 26 further includes a light beam deflecting portion such as a weak concave lens.

In the present embodiment, as illustrated in FIG. 28, for example, there may be provided a light beam deflecting portion 49 such as a weak concave lens (field lens), which is disposed between the surface light source 9 and the objective lens 7 and which deflects the light beam of the illumination light emitted from the surface light source 9 in a direction away from the optical axis of the objective lens 7 so as to be incident on the objective lens 7.

Figure 29:
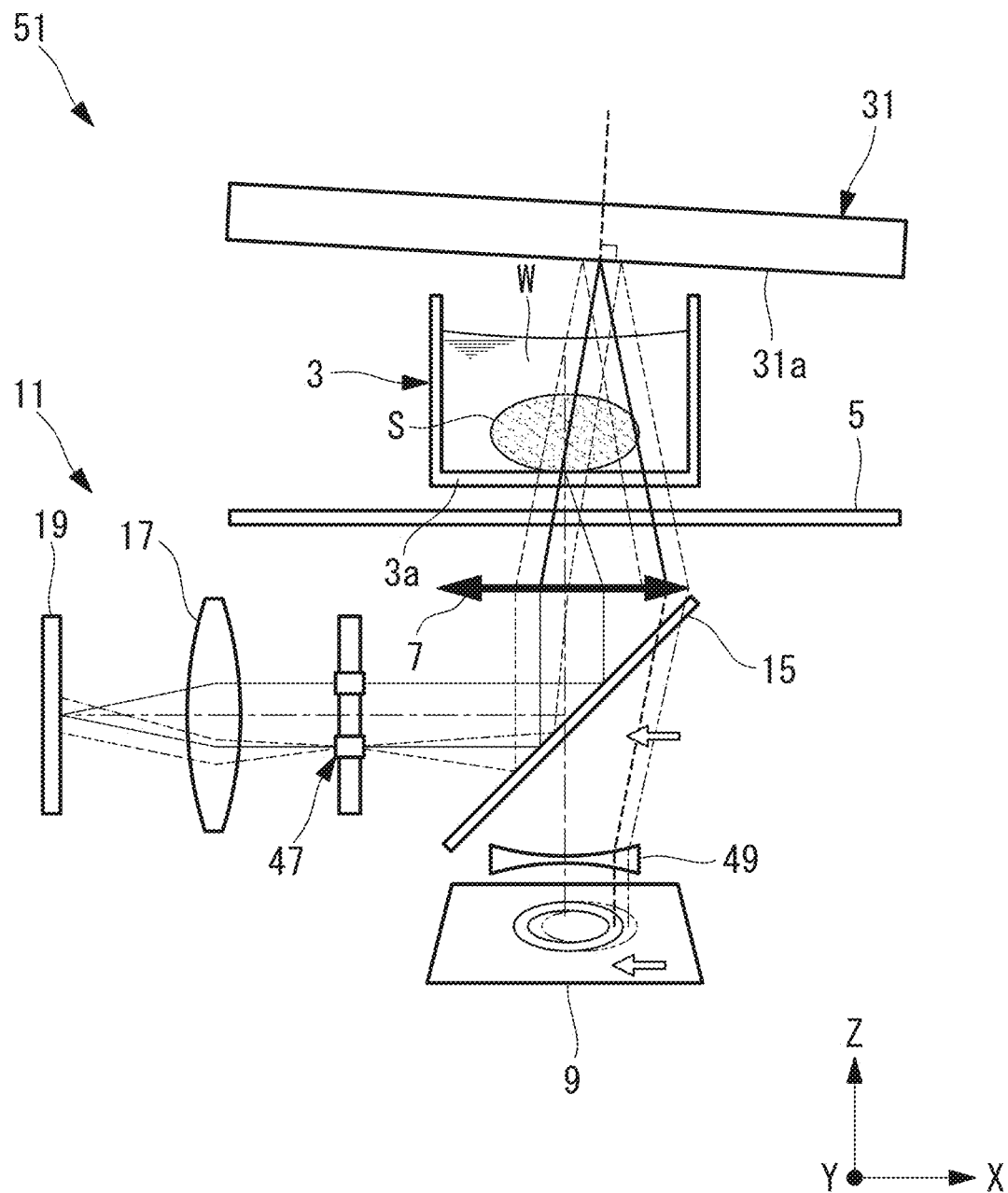
FIG. 29 is a diagram illustrating an example of an optical path of illumination light and observation light when a light emitting region of a surface light source has been changed in the observation device in FIG. 28.

In this case, as illustrated in FIG. 29, the recording and calculation unit 23, by executing a program, corrects the light emission pattern of the surface light source 9 on the basis of the light emission pattern of the surface light source 9 and at least one of the brightness, contrast, and the relationship between the number of pixels and the luminance of an image acquired by the imaging optical system 11 with the light emission pattern, such that the observation light from the specimen S is reflected by the light separating portion 15 and passes through the phase film 47.

With this configuration, the illumination light deflected by the light beam deflecting portion 49 can be efficiently applied to the specimen S by the objective lens 7.

Although the embodiments of the present invention have been described above in detail with reference to the drawings, the specific configuration is not limited to these embodiments, and includes design changes and the like within a scope not deviating from the gist of the present invention. For example, the present invention is not limited to application to each of the above-described embodiments and modifications, and may be applied to an embodiment in which these embodiments and modifications are combined as appropriate, and is not particularly limited.

As a result, the above-described embodiments lead to the following aspect.

An aspect of the present invention is directed to an observation device including an objective lens that is disposed below a specimen container that contains a specimen and that collects light from the specimen through a bottom portion of the specimen container; a surface light source that is arranged at a pupil position of the objective lens in an optical path of illumination light to be incident on the objective lens or at a vicinity of a position conjugate with the pupil position, that makes illumination light transmitted through the bottom portion from below incident on the specimen container and can changes a light emission pattern related to a light emission position and a light emission range of the illumination light in a direction intersecting an emission optical axis, an imaging optical system that captures light from the specimen generated by the specimen being irradiated with the illumination light from the surface light source and focused by the objective lens below the specimen container; and a control unit that corrects the light emission pattern of the surface light source on a basis of a current light emission pattern of the surface light source and at least one of a brightness, contrast, and a relationship between the number of pixels and a luminance of an image acquired by the imaging optical system with the light emission pattern of the surface light source.

According to this aspect, the illumination light emitted upward from the surface light source below the specimen container is transmitted through the bottom portion of the specimen container to irradiate the specimen, and the light from the specimen focused by the objective lens through the bottom of the specimen container below the specimen is captured by the imaging optical system. By performing illumination and image capture through the bottom portion of the specimen container, an available specimen container does not have to have a side surface limited in shape as in the configuration where illumination light is incident on the container from the side, and the apparatus can be reduced in size by not disposing the optical system above the specimen.

In this case, specimens can be image-captured with high definition by using the control unit to correct the light emission pattern of the illumination light from the surface light source on the basis of the current light emission pattern of the surface light source and at least one of the brightness, contrast, and the relationship between the number of pixels and the luminance of an image acquired by the imaging optical system with the light emission pattern of the surface light source. Therefore, it is possible to deal with specimen containers of various shapes and to acquire a detailed image of the specimen in a small space.

In the above aspect, the apparatus may further include a phase modulation element disposed at a pupil position of the objective lens in an optical path of the imaging optical system, in which the control unit corrects the light emission pattern of the surface light source such that the light from the specimen collected by the objective lens is incident on the phase modulation element.

With this configuration, light from the specimen that has passed through the phase modulation element can be captured by the imaging optical system.

In the above aspect, the phase modulation element may include a phase film that phase-modulates the light from the specimen.

With this configuration, light from the specimen that has been phase-modulated by the phase film can be captured by the imaging optical system, and an image of the specimen with bright-dark contrast can be acquired. Consequently, a specimen such as a transparent cell can be observed with high definition without labeling.

In the above aspect, the phase modulation element may include a dimming member that dims the light from the specimen so as to suppress passage of the illumination light applied to the specimen.

With this configuration, scattered light or diffracted light generated in the specimen irradiated with the illumination light can be captured by the imaging optical system, and a high-contrast image of the specimen can be acquired. Thus, a specimen such as a transparent cell can be observed with high definition without labeling.

In the above aspect, the observation device may further include a reflecting member that is disposed above the specimen and that reflects the illumination light from the surface light source toward the specimen, in which the imaging optical system captures below the specimen the illumination light reflected by the reflecting member that has been transmitted through the specimen.

With this configuration, it is possible to perform transmission illumination by only disposing the reflecting member without disposing the light source above the specimen container. Thereby, it is possible to secure a space above the specimen and to easily observe a specimen such as a transparent cell.

In the above aspect, the observation device may further include a light separating portion that separates the illumination light and the light from the specimen, in which, while radiating the specimen with the illumination light from the surface light source through the objective lens, coaxial epi-illumination in which the light from the specimen, which has been collected by the objective lens and separated from the illumination light by the light separating portion, is captured by the imaging optical system may be configured.

With such a configuration, a space where illumination light enters the specimen and a space where light from the specimen is focused can be made common, and a specimen container having a small bottom portion can be used.

In the above aspect, the light separating portion may include a half mirror.

With this configuration, the illumination light and the light from the specimen can be separated in accordance with the transmittance and reflectance of the half mirror. In addition, any surface light source can be used with the invention.

In the above aspect, the light separating portion may include a polarizing beam splitter.

With this configuration, the polarizing beam splitter can separate the illumination light and the light from the specimen in accordance with a polarization component. This is particularly effective when a surface light source having a polarization characteristic such as a liquid crystal screen or a laser diode is used.

In the above aspect, the light separating portion may include a dichroic mirror.

With such a configuration, the dichroic mirror can separate the illumination light and the light from the specimen in accordance with wavelength. This is particularly effective when observing fluorescence or luminescence.

In the above aspect, the observation device may further include a light beam deflecting portion that is disposed between the surface light source and the objective lens, and that deflects a light beam of the illumination light emitted from the surface light source in a direction away from an optical axis of the objective lens and that causes the light beam to enter the objective lens.

With such a configuration, the illumination light deflected by the light beam deflecting portion can be efficiently illuminated on the specimen by the objective lens.

According to the present invention, it is possible to deal with containers of various shapes and to acquire a detailed image of a specimen in a small space.

REFERENCE SIGNS LIST 1,41,51 observation device
3 specimen container
7 objective lens
9 surface light source
11 imaging optical system
15 light separating portion
23 recording and calculation unit (control unit)
31 reflecting member
43 light-blocking film (dimming member, phase modulation element)
47 phase film (phase modulation element)
49 light beam deflecting portion
S specimen

The invention claimed is:

1. An observation device comprising:
an objective lens that is disposed below a specimen container that contains a specimen, the objective lens being configured to collect light from the specimen through a bottom portion of the specimen container;
a surface light source that is arranged at a pupil position of the objective lens in an optical path of illumination light to be incident on the objective lens or at a vicinity of a position conjugate with the pupil position and that makes illumination light transmitted through the bottom portion from below incident on the specimen container, the surface light source being configured to change a light emission pattern of the illumination light in a direction intersecting an emission optical axis, the surface light source comprising a plurality of light-emitting elements, the light emission pattern being changed by changing a light emission position of the plurality of light-emitting elements;
an imaging optical system that captures light from the specimen, generated by the specimen being irradiated with the illumination light from the surface light source and focused by the objective lens below the specimen container; and
a controller configured to correct an initial light emission pattern of the surface light source to obtain the light emission pattern of the surface light source on a basis of at least one of a brightness, contrast, and a relationship between a number of pixels and a luminance of an image acquired by the imaging optical system with the initial light emission pattern.

2. The observation device according to claim 1, further comprising a phase modulation element disposed at a pupil position of the objective lens in an optical path of the imaging optical system,
wherein the controller is configured to correct the light emission pattern of the surface light source such that the light from the specimen collected by the objective lens is incident on the phase modulation element.

3. The observation device according to claim 2, wherein the phase modulation element comprises a phase film that phase-modulates the light from the specimen.

4. The observation device according to claim 2, wherein the phase modulation element comprises a dimming member that dims the light from the specimen so as to suppress passage of the illumination light applied to the specimen.

5. The observation device according to claim 1, further comprising a reflecting member that is disposed above the specimen, the reflecting member being configured to reflect the illumination light from the surface light source toward the specimen,
wherein the imaging optical system captures, below the specimen, the illumination light that has been reflected by the reflecting member and then transmitted through the specimen.

6. The observation device according to claim 1, further comprising a light separating portion configured to separate the illumination light and the light coming from the specimen,
wherein, the specimen is irradiated with the illumination light from the surface light source through the objective lens, and coaxial epi-illumination in which the light from the specimen, which has been collected by the objective lens and separated from the illumination light by the light separating portion, is captured by the imaging optical system.

7. The observation device according to claim 6, wherein the light separating portion comprises a half mirror.

8. The observation device according to claim 6, wherein the light separating portion comprises a polarizing beam splitter.

9. The observation device according to claim 6, wherein the light separating portion comprises a dichroic mirror.

10. The observation device according to claim 6, further comprising a light beam deflecting portion that is disposed between the surface light source and the objective lens, the light beam deflecting portion being configured to deflect a light beam of the illumination light emitted from the surface light source in a direction away from an optical axis of the objective lens and cause the light beam to enter the objective lens.

11. An observation device comprising:
an objective lens that is disposed below a specimen container that contains a specimen, the objective lens being configured to collect light from the specimen through a bottom portion of the specimen container;
a surface light source that is arranged at a pupil position of the objective lens in an optical path of illumination light to be incident on the objective lens or at a vicinity of a position conjugate with the pupil position and that makes illumination light transmitted through the bottom portion from below incident on the specimen container, the surface light source being configured to change a light emission pattern related to a light emission position and a light emission range of the illumination light in a direction intersecting an emission optical axis;

an imaging optical system that captures light from the specimen, generated by the specimen being irradiated with the illumination light from the surface light source and focused by the objective lens below the specimen container;

a controller configured to correct an initial light emission pattern of the surface light source to obtain the light emission pattern of the surface light source on a basis of at least one of a brightness, contrast, and a relationship between a number of pixels and a luminance of an image acquired by the imaging optical system with the initial light emission pattern; and a reflecting member that is disposed above the specimen and that reflects the illumination light from the surface light source toward the specimen;

wherein the imaging optical system captures, below the specimen, the illumination light that has been reflected by the reflecting member and then transmitted through the specimen.

* * * * *